US006869779B1

(12) United States Patent
Yamada et al.

(10) Patent No.: US 6,869,779 B1
(45) Date of Patent: Mar. 22, 2005

(54) NUCLEIC ACID SEQUENCE FOR POTENTIATING THE EXPRESSION OF USEFUL GENE AND METHOD THEREFOR

(75) Inventors: Osamu Yamada, Hyogo (JP); Hiroshi Yoshida, Osaka (JP); Jing Zhang, Osaka (JP)

(73) Assignee: FUSO Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/763,836

(22) PCT Filed: Jul. 7, 1999

(86) PCT No.: PCT/JP99/03682

§ 371 (c)(1),
(2), (4) Date: Jun. 8, 2001

(87) PCT Pub. No.: WO00/12691

PCT Pub. Date: Mar. 9, 2000

(30) Foreign Application Priority Data

Aug. 27, 1998 (JP) ............................................. 10-241367

(51) Int. Cl.[7] .......................... C12P 21/00; C12N 15/71; C12N 15/85; C07H 21/04
(52) U.S. Cl. .................. 435/70.1; 435/320.1; 536/24.1; 536/23.1; 424/93.7
(58) Field of Search ............................. 435/320.1, 70.1; 536/24.1, 23.1; 424/93.7

(56) References Cited

FOREIGN PATENT DOCUMENTS

| JP | 7-69899 | 3/1995 |
|---|---|---|
| JP | 10-327871 | 12/1998 |
| WO | WO 98/11241 | 3/1998 |

OTHER PUBLICATIONS

Verma et al., Gene therapy–promises, problems and prospects, 1997, Nature, vol. 389, pp. 239–242.*
Marshall, gene therapy's growing pains, 1995, Science, vol. 269, pp. 1050–1055.*
Orkin et al., Report and recommendations of the panel to assess the NIH investment in research gene therapy, 1995, NIH.*
Borman et al., Picornavirus internal ribosome entry segments: comparison of translation efficiency and the requirements for optimal internal initiation . . . , 1995, Nucleic Acids Reseach, vol. 23, pp. 3656–3663.*
Yoo et al., 5' end–dependent translation initiation of hepatitis C viral RNA and the presence of putative positive and negative translational control elements within 5' untranslated region, 1992, Virology, vol. 191, pp. 889–899.*
Collier et al., Translation efficiencies of the 5' untranslated region from representatives of the six major genotypes of hepatitis C virus using a novel bicistronic reporter assay system, 1998, Journal of General Virology, vol. 79, pp. 2359–2366.*

Accession AB016785, Direct Submission, Virology 261 (2), 263–270 (1999).*
Brown et al., Secondary structure of the 5' nontranslated regions of hapatitis C virus and positive genomic RNAs, 1992, Nucleic Acids Research, vol. 20, pp. 5041–5045.*
Dirks et al., Dicistronic transcription units for gene expression in mammalian cells, 1993, Gene, vol. 128, pp. 247–249.
Fukushi et al., The sequence element of the internal ribosome entry site and a 25–kilodalton cellular protein contribute to efficient internal initiation of translation of hepatitis C virus RNA, 1997, Journal of Virology, pp. 1662–1666.
Laporte et al., Comparative analysis of translation efficiencies of hepatitis C virus 5' untranslated regions among intraindividual quasispecies present in chronic infection . . . , 2000, Journal of Virology, pp. 10827–10833.
Rijnbrand et al., The Influence of AUG Codons in the Hepatitis C Virus 5' Nontranslated Region on Translation and Mapping of the Translation Initiation Window, Virology, 226:47–56 (1996).
Genbank Accession No. AF054249, Yanagi et al., 1998.
Genbank Accession No. D00832.
Vennema et al., "Enhancement of the Vaccina Virus/Phage T7 RNA Polymerase Expression System Using Encephalomyocarditis Virus 5'–Untranslated Region Sequences," Gene 108:201–209 (1991).
Yanagi et al., "Transcripts of a Chimeric cDNA Clone of Hepatitis C Virus Genotype 1b Are Infectious in Vivo," Virology 244:161–172 (1998).
Ali et al., "The La Antigen Binds 5' Noncoding Region of the Hepatitis C Virus RNA in the Context of the Initiator AUG Codon and Stimulates Internal Ribosome Entry Site–Mediated Translation", Proc. Natl. Acad. Sci. USA, 94(2249–2254) 1997.
Brown et al., "Secondary Structure of the 5' Nontranslated Regions Of Hepatitis C Virus And Pestivirus Genomic RNAs", Nucleic Acids Research, 20:19(5041–5045) 1992.
Bukh et al., "Sequence Analysis of the 5' Noncoding Region of Hepatitis C Virus", Proc. Natl. Acad. Sci. USA, 89:11(4942–4946)1992.

(List continued on next page.)

Primary Examiner—David Guzo
Assistant Examiner—Daniel M. Sullivan
(74) Attorney, Agent, or Firm—Marshall, Gerstein & Borun LLP

(57) ABSTRACT

Nucleic acid sequences for enhancing expression of a useful gene, which car increase the production of the gene product by enhancing gene expression, comprising a 5'-untranslated region of a viral gene or a fragment or a variant thereof, vectors comprising the nucleic acid sequence, host cells transformed or transfected with the vector, and methods for enhancing expression of a useful gene with the vector are provided. In addition, the sequences of the present invention can be utilized for screening an agent that interacts with IRES elements, and of an IRES-dependent translation initiator, as well as for treating diseases resulting from reduction of cap-dependent mRNA translation or reduction of IRES activity, and for determining severity of hepatitis C.

23 Claims, 13 Drawing Sheets

OTHER PUBLICATIONS

Buratti et al., "Functional Analysis of the Interaction Between HCV 5'UTR and Putative Subunits of Eukaryotic Translation Initiation Factor eIF3," *Nucleic Acids Research*, 26:113(3179–3187)1998.

Dirks et al., "Dicistronic Transcription Units For Gene Expression In Mammalian Cells", *Gene*, 128:2(247–249)1993.

Fukishi et al., "The Sequence Element of the Internal Ribosome Entry Site and a 25–Kilodalton Cellular Protein Contribute to Efficient Internal Initiation of Translation of Hepatits C Virus RNA", *Journal of Virology*, 71:2(1662–1666)1997.

Gaines et al., "pIRES–CD4t, A Discistronic Expression Vector For MACS–or FACS–based Selection Of Transfected Cells", *Biotechniques*, 26:4(683–688)1999.

Hahm et al., "Hetergenous Nuclear Ribonucleoprotein L Interacts with the 3' Border of the Internal Ribosomal Entry Site of Hepatitis C Virus", *Journal of Virology*, 72:11(8782–8788)1998.

Hijikata et al., "Gene Mapping of the Putative Structural Region of the Hepatitis C Virus Genome by in vitro Processing Analysis", *Proc. Natl. Acad. Sci. USA*, 88(5547–5551)1991.

Honda et al., "A Phylogenetically Conserved Stem–Loop Structure at the 5' Border of the Internal Ribosome Entry Site of Hepatitis C Virus Is Required for Cap–Independent Viral Translation", *Journal of Virology*, 73:2(1165–1174)1999.

Ito et al., "The 3'–Untranslated Region of Hepatitis C Virus RNA Enhances Translation for an Internal Ribosomal Entry Site", *Journal of Virology*, 72:11(8789–8796)1998.

Jackson et al., "Internal Initiation of Translation of Picornavirus RNAs", *Molecular Biology Reports*, 19(147–159)1994.

Jackson et al., "Internal Initiation of Translation in Eukaryotes: The Picornavirus Paradigm and Beyond", *RNA*, 1(985–1000).

Kozak, M. "An Analysis of 5'–Noncoding Sequences from 699 Vertebrate Messenger RNAs", *Nucleic Acids Research*, 15:20(8125–8148)1987.

Martinez–Salas et al., "Functional Interactions In Internal Initiation Directed By Viral and Cellular IRES Elements", *Journal of General Virology*, 82(973–984)2001.

Paulin et al., "A Single Nucleotide Change in the c–myc Internal Ribosme Entry Segment Leads to Enhanced Binding of a Group of Protein Factors", *Nucleic Acids Research*, 26:13(3097–3103)1998.

Pestova et al., "A Prokaryotic–like Mode of Cytoplasmic Eukaryotic Ribosome Binding To the Initiation Codon During Internal Translation Initiation of Hepatitis C and Classical Swine Fever Virus RNAs", *Genes Dev.*, 12:1(67–83)1998.

Renyolds et al., "Unique Features of Internal Initiation of Hepatitis C Virus RNA Translation", *EMBO Journal*, 14:23(6010–6020)1995.

Sizova et al., "Specific Interaction of Eukaryotic Translation Initiation Factor 3 eith the 5' Nontranslated Regions of Hepatitis C Virus and Classical Swine Fever Virus RNAs", *Journal of Virology*, 72:6(4775–4782).

Tsukiyama–Kohara et al., "Internal Ribosome Entry Site Within Hepatitis C Virus RNA", *Journal of Virology*, 66:3(1476–1483)1992.

International Search Report, International Application No.: PCT/JP99/03682, International Searching Authority/Japanese Patent Office (with Japanese language search report attached).

* cited by examiner

```
5'-UTR₃₄₁  GCCAGCCCCC TGATGGGGGC GACACTCCAC CATAGATCAC TCCCCTGTGA  50
5'-UTR₃₄₂  GCCAGCCCCC TGATGGGGGC GACACTCCAC CATAGATCAC TCCCCTGTGA  50

5'-UTR₃₄₁  GGAACTACTG TCTTCACGCA GAAAGCGTCT AGCCATGGCG TTAGTATGAG  100
5'-UTR₃₄₂  GGAACTACTG TCTTCACGCA GAAAGCGTCT AGCCATGGCG TTAGTATGAG  100

5'-UTR₃₄₁  TGTCGTGCAG CCTCCAGG[A]C CCCCCCTCCC GGGAGAGCCA TAGTGGTCTG  150
5'-UTR₃₄₂  TGTCGTGCAG CCTCCAGG[C]C CCCCCCTCCC GGGAGAGCCA TAGTGGTCTG  150

5'-UTR₃₄₁  CGGAACCGGT GAGTACACCG GAATTGCCAG GACGACCGGG TCCTTTCTTG  200
5'-UTR₃₄₂  CGGAACCGGT GAGTACACCG GAATTGCCAG GACGACCGGG TCCTTTCTTG  200

5'-UTR₃₄₁  GATCAA[·]CCC GCTCAATGCC TGGAGATTTG GGCGTGCCCC CGCGAGACTG  249
5'-UTR₃₄₂  GATCAA[T]CCC GCTCAATGCC TGGAGATTTG GGCGTGCCCC CGCGAGACTG  250

5'-UTR₃₄₁  CTAGCCGAGT AGTGTTGGGT CGCGAAAGGC CTTGTGGTAC TGCCTGATAG  299
5'-UTR₃₄₂  CTAGCCGAGT AGTGTTGGGT CGCGAAAGGC CTTGTGGTAC TGCCTGATAG  300

5'-UTR₃₄₁  GGTGCTTGCG AGTGCCCCGG GAGGTCTCGT AGACCGTGCA CC          341
5'-UTR₃₄₂  GGTGCTTGCG AGTGCCCCGG GAGGTCTCGT AGACCGTGCA CC          342
```

Fig. 5

NUCLEIC ACID SEQUENCE FOR POTENTIATING THE EXPRESSION OF USEFUL GENE AND METHOD THEREFOR

FIELD OF THE INVENTION

The present invention relates to nucleic acid sequences for enhancing expression of a useful gene in an expression vector, vectors comprising a nucleic acid sequence for enhancing expression of a useful gene, and host cells transformed or transfected with one of the vectors described above as well as methods for preparing a useful gene product using such vectors. Methods are further provided for enhancing expression of a useful gene with one of the vectors described above. More specifically, the present invention relates to nucleic acid sequences for enhancing expression of a useful gene that can increase in vivo and in vitro production of a gene product, allowing advantageous application to various experiments as well as gene therapies in combination with such a promoter that is specific to an internal organ or a tumor but has not been likely to come into practical use due to its low activity. In addition, the nucleic acid sequences for enhancing expression of a useful gene may be used for screening of an agent that interacts with IRESs, and of a translation initiator, and for the treatment and diagnosis of, and prophylaxis against, various diseases.

BACK GROUND OF THE INVENTION

The mechanisms involving in initiation of mRNA translation are known to be either cap-dependent or cap-independent. The 5'-terminal structure of prokaryotic mRNAs is pppN while eukaryotic mRNAs have a cap structure ((7-MeG)-5'-ppp-5'-(G/A)-3'-p-) (G or A, with possibly methylated ribose) at their 5'-end. This cap structure plays a role in the transportation of mRNA from nuclei to cytoplasm, protecting mRNAs from RNase. In the cytoplasm of eukaryotic cells, binding of the cap-binding protein complex (also referred to as eukaryotic initiation factor 4F (eIF-4F)) to the cap structure promotes the entry of a 40S ribosomal subunit into the mRNA 5'-end, and then the ribosome within the mRNA 5'-end moves along the mRNA toward the 3'-end, scanning the 5'-untranslated region of about 100 bases in length, then peptide synthesis is performed in many cases, using the first AUG sequence that the ribosome encounters as the initiation codon.

However, an eukaryotic mRNA has been found which uses a different mechanism from the cap-dependent translation mechanism described above. Although the eukaryotic mRNAs were known to have a cap structure at their 5'-end, it has been reported that the 5'-end of *poliovirus* mRNA is uncapped; instead, its structure is merely pU (Nomoto, A. et al, *Proc. Natl. Acad. Sci. USA,* 74, 5345, 1977). The entire primary structure of *poliovirus* RNAs has then been elucidated with a detailed genetic map thereof (Kitamura, N. et al., *Nature,* 291, 547, 1981). Consequently, it was indicated that the initiation AUG codon is located at position 743 base of mRNA and is preceded by some AUG triplets. Such a mRNA structure has been revealed to be commonly found in other members belonging to the same family (family Picornaviridae) as the *poliovirus*. Furthermore, the cap-independent mechanism for translation initiation (internal initiation mode) has been demonstrated for *picornavirus* es through the experiments with *poliovirus* RNA (Pelletier, J. et al, *Nature,* 334, 320, 1988) and encephalomyocarditis virus (EMCV) RNA (Jang, S. K. et al., *J. Virol.,* 62, 2636, 1988), revealing the recognition of base sequences in the 5'-untranslated region (5'-UTR) of mRNA by ribosomes and the internal entry of the ribosomes which occurs at an internal site(s) within the 5'-untranslated region. The region required for the entry of ribosomes has been called the internal ribosomal entry site (IRES).

*Picornavirus* RNA possesses a 5'-untranslated region of about 600–1200 bases in length, of which a region of about 450 bases has IRES activity. The *picornavirus* IRES presents a common structure, i.e., a pyrimidine-rich tract ((C/U)x) and a following short sequence of about 7 bases in length containing AUG. A random base sequence (Ny) of 10–20 bases in length is located between the pyrimidine-rich tract and the short sequence (Jang, S. K. et al., in Translationally Regulated Genes in Higher Eukaryotes, Thach, R. E. ed., 292–309, Karger, 1990). The pyrimidine-rich tract means a region that contains at least 4, 5 or more continuous pyrimidine bases. The (CIU)x-Ny-AUG unit is expected to be one of essential structures for IRESs, in fact, deletions of base sequences containing AUG diminish IRES activities which are completely lost with further deletion of the entire region of (C/U)x (Kuge, S. et al., *J. Virol.,* 61, 1478, 1987; Iizuka, N. et al., *J. Virol.,* 65, 4867, 1991). In general, the region of (C/U)x sequence is called "BoxA" while the region containing AUG of about 7 bases in length is called "BoxB". Since these boxes present complementarity to a sequence at the 3'-end of the 18S ribosome RNA (rRNA), IRES is regarded as having a similar function to the Shine-Dalgarno sequence (SD sequence) of prokaryotic mRNAs (Pilipenko, E. V. et al., *Cell,* 68, 119, 1992).

*Picornavirus* IRES is classified into two types: type I IRESs are found in enteroviruses and rhinoviruses, whereas type II IRESs are found in *cardioviruses* and *aphthoviruses*. *Hepatovirus* IRESs are considered to be an analog of the type II IRES.

With respect to the type I IRES, the ribosome scans a region downstream of (C/U)x-Ny-AUG unit and initiates peptide synthesis at the first AUG which serves as the initiation codon. Insertion of an AUG sequence at a position upstream of the initiation AUG codon actually results in significantly inhibited replication in the virus (Kuge, S. et al., *J. Virol.,* 63, 1069, 1989; Kuge, S. et al., *J. Mol. Biol.,* 207, 175, 1989). For the type II IRES elements, on the other hand, AUG within the (C/U)x-Ny-AUG unit is used as the initiation codon.

In 1989, hepatitis C virus (hereinafter, referred to as HCV) that is a plus single-stranded RNA virus has been reported as a causative virus of non-A, non-B viral post-transfusion hepatitis (Choo, Q. et al., *Science,* 244, 359, 1989). Chronic infection of this virus leads to liver cirrhosis and hepatocellular carcinoma at a high incidence, which has been clinically problematic (Saito, I. et al., *Proc. Natl. Acad. Sci. USA,* 87, 6547, 1990). To date, the entire base sequences of at least 40 HCV genome subtypes have been identified. The genome RNA of about 9600 bases in length comprises a 5'-untranslated region of about 341 bases in length, a coding region that codes for a polypeptide of 3008–3037 amino acid residues and a 3'-untranslated region of 200–300 bases in length, where the 3'-untranslated region terminates in a structure called 3'X of 98 bases in length following the poly U/C tract. The polypeptide of this virus is analogous to that found in *flaviviruses* and *pestiviruses* (Kato, N. et al., *Proc. Natl. Acad. Sci. USA,* 87, 9524, 1990; Takamizawa, A. et al., *J. Virol.,* 65, 1105, 1991) and carries the viral proteins in the following order from the N-terminus designated as: C/core, E1, E2, p7, NS2, NS3, NS4A, NS4B, and NS5A. The E2 region corresponds to a non-structural protein NS1 in *flavivirus* and an envelope protein E2 in *pestivirus*. HCV had been considered as E2/NS1 but is recently considered as E2, because similar characteristics have been shown to *pestiviruses*, and is expected to be an envelope protein. It has been reported that, based on the sequence identity, there are 6 to 11 genotypes of the virus.

According to the virological classification, HCV belongs to the family Flaviviridae, together with GB virus/hepatitis G virus that have been identified later. It has been discovered that an internal ribosome entry site (IRES) exists in the 5'-untranslated region of the base sequence of HCV, which is found, for example, in *picornavirus* mRNAs, unlike usual cap-dependent translation of the eukaryotic mRNAs into the proteins (Tsukiyama-Kohara, K. et al., *J. Virol.*, 66, 1476, 1992). This IRES exhibits its activity with a shorter base sequence than the *picornavirus* IRES does, and thus the HCV IRES is expected to have a secondary structure which is completely distinct from that of *picornavirus* (Tsukiyama-Kohara, K. et al., *J. Virol.*, 66, 1476, 1992; Brown, E. A. et al. *Nucl. Acid Res.*, 20, 5041, 1992). On the other hand, base A sequences corresponding to BoxA and BoxB have been observed within the region of HCV IRES, which are complementary to the 3'-end of 18S rRNA (Nomoto, A. et al., in Viral Hepatitis and Liver Disease, Nishioka, K., Suzuki, H., Mishiri, S., Oda, T. eds., 118, Springer-Verlag, 1994). See, FIG. 1 for the putative structure of the region of HCV IRES. In the figure, the thick line indicates the pyrimidine-rich tract which corresponds to BoxA and the sequence of about 7 bases in length containing AUG which corresponds to BoxB, whilst the double line indicates the pyrimidine-rich tract located upstream of BoxA, additionally, binding-sites of the trans factors (described later) are encircled.

*Pestivirus* (family Fraviviridae) IRESs, the IRES activity of which has recently been identified, have no base sequence corresponding to BoxA and BoxB, although their secondary structures are similar to those of HCV IRESs (Brown, E. A. et al., *Nucl. Acid Res.*, 20, 5041, 1992). Plant virus IRESs discovered one after another in recent years exhibit the activity with a yet shorter base sequence and no part is conserved corresponding to BoxA and BoxB. These results suggest that the two boxes are not necessarily essential for IRES activity. Thus, a simply standarized mechanism such as the cap-dependent translation initiation may not be enough to explain a variety of modes of expressing IRES functions.

Translation initiation in HCV is different from that during the cap-dependent protein synthesis found in the majority of eukaryotic mRNAs in respect that it depends on IRES located in the 5'-site. A single, long polypeptide synthesized in an IRES-dependent manner is processed into proteins by a host signal peptidase and two kinds of viral proteases. These proteins are subjected to further individual processing by the signal peptidase, glycosylation and phosphorylation by a viral protein, thus they acquire various characteristics required for viral replication and for accomplished infection.

The long HCV 5'-UTR of about 341 bases in length is similar to those of pestiviruses or *picornaviruses*, different from those in *flaviviruses* because it contains multiple (2 to 5) AUG sequences that are not served as the initiation codon and may form a complicated secondary structure (Han, J. H. et al., *Proc. Natl. Acad. Sci. USA*, 88, 1711, 1991; Brown, E. A. et al. *Nuceic Acid. Res.*, 20, 5041, 1992).

Many investigators have made reports on the region of HCV IRES with various different conclusions. Such inconsistencies are speculated to result from RNA structures and translation systems used for the experiments. Using in vitro transfection in the rabbit reticulocyte lysate or DNA transfection into cultured cells which are infected with a vaccinia virus that co-expresses T7 RNA polymerase, a stretch extending from about 40 bases of 5'-UTR to about 30 bases of the coding region may be considered as the region corresponding to IRES (Reynolds, J. E. et al., *EMBO J*, 14, 6010, 1995). In addition, RNA transfection into cultured cells has proven that the 5' boundary of HCV IRES resides between base 28 and base 45 (Kamoshita, N. et al., *Virology*, 233, 10, 1997). Furthermore, an analysis on cell-free systems provided such a result that the 3' boundary thereof resides between base 370 and base 516 rather than residing within several ten bases in the coding region. This result is consistent with the report that two thirds of a portion of the core protein (the protein coded by the sequences in the coding region immediately downstream of the 5'-untranslated region) on the side of the N-terminus accelerate IRES activities (Lu, H. -H. et al, *Proc. Natl. Acad. Sci. USA*, 93, 1412, 1996), however, the possibility of this region being important for the structure of RNA cannot be completely denied.

Many molecules involved in the cap-dependent translation initiation are mobilized for the expression of the IRES functions, besides, it has been considered that other molecules derived from the host cells (trans factors) are also required (Scheper, G. C. et al., *J. Biol. Chem.*, 267, 7269, 1992). This fact is readily presumed because the expression of ERES functions is species-, tissue- and cell-specific.

According to comparative experimental reports on viral IRES activities by using wheat germ lysates, rabbit reticulocyte lysates (RRL), and HeLa cell lysates, which are known as a cell-free protein synthetic system for capped mRNA, *picornavirus* IRES exhibits no activity in wheat germ lysates. On the other hand, in RRL, EMCV IRES reportedly exhibits a high activity while *poliovirus* IRES has a weak activity, and the *poliovirus* IRES activity in RRL is recovered by addition of HeLa cell lysate (Brown, B. A. et al., *Virology*, 97, 396, 1979; Dorner, A. J. et al., *J. Virol.*, 50, 507, 1984). Moreover, it has been suggested that these viral IRESs all exhibit a high activity in HeLa cell lysates, whilst only IRES of hepatitis A virus (HAV) has a low activity even in HeLa cell lysates (Glass, M. J. et al, *Virology*, 193, 1047, 1993). These results provide clear evidence that the expression of IRES functions requires a cluster of molecules derived from the host cell other than the initiators that may be used by the capped mRNA. In addition, it is also clear that the quality and quantity of the molecules required for the expression of the functions may vary depending on the type of the IRES.

Further, analysis using UV cross-linking method (a method in which nucleic acids and proteins bound thereto are cross-linked with UV light to determine a binding protein(s)) has indicated that many molecules derived from the host cell may bind to any IRES. Moreover, it has been revealed that, besides conformation of RNAs, the trans factors that act in an IRES-specific manner may play important roles in initiation of translation. More specifically, two types of IRES binding proteins are known as host molecules that accelerate activity of the *picornavirus* IRES: La (52 kDa) and PTB (polypyrimidine tract binding protein, 57 kDa) (Meerovitch, K. et al, *J. Viol.*, 67, 3798, 1993; Hellen, C. V. T. et al., *Proc. Natl. Acad. Sci. USA*, 90, 7642, 1993; Borman, A. et al., *J. Gen. Virol.* 74, 1775, 1993). La is known as an antigenic protein in autoimmune diseases, and is a transcription termination factor for RNA polymerase III. Further, PTB is a cofactor of RNA splicing. These proteins are localized in the nuclei of cells and actually involved in intranuclear reactions. However, it has been reported that infection with, for example, *poliovirus* results in transportation of La from nuclei to cytoplasm (Meerovitch, K. et al., *J. Viol.,* 67, 3798, 1993), and the transportation is reportedly associated with the initiation of translation that is a reaction in cytoplasm.

The requirement of PTB and La for various IRESs has been studied, and to date, it has been suggested that the requirement of PTB for *picornavirus* IRES is high whereas that for HCV IRES is significantly low (Kaminski, A. et al., RNA, 1, 924, 1995), and also that HCV requires lower amount of La than *poliovirus* does. On the contrary, other report has suggested that PTB binds to the HCV IRES at three sites and such binding is essential for IRES functions (Ali, N. et al., *J. Viol.,* 69, 6367, 1995), and that the La recognizes the RNA structure containing the initiation AUG, thus activation is resulted (Ali. N. et al., *Proc. Natl. Acad. Sci. USA,* 94, 2249, 1997). These kinds of experiments are carried out by using cell-free protein synthetic systems in which PTB is eliminated as much as possible, wherein specific antibodies or PTB-binding RNA fragments are used for the purpose of eliminating the PTB. Therefore, in cases where PTB is forming a complex with other molecules (Toyoda, H. et al., *Arch. Virol.,* 138, 1, 1994), the whole complex may be entirely eliminated. Moreover, elimination of ribosomes should also be considered because many PTBs are known to be bound thereto. Further investigations should thus be conducted on the requirement of trans factors for IRES, however, it is expected that the trans factors required for IRES may vary depending on each IRES, and that mechanisms leading to the expression of the functions may vary from IRES to IRES. Novel IRES-associated factors may possibly be present in HCV, and in fact, a protein in HeLa cell p25, has been reported which recognizes a secondary structure in 5'-untranslated region, the binding affinity of which is correlated with the efficiency of translation (Fukushi, S. et al., *J. Virol.,* 71, 1662, 1997).

Genetic engineering has been used to produce various proteins and peptides to date. For example, various substances including insulin, interferons, erythropoietin, mannan-binding protein, conglutinin, neurosin, and the like have been produced in microbial cells including *Escherichia coli* and animal cells such as CHO cells.

When useful gene products from animals are genetically engineered, usage of microbial cell hosts such as *Escherichia coli, Bacillus subilis,* or *Saccharomyces cerevisiae* may often cause problems such as failure of gene expression or loss of activity due to an improper tertiary structure of a gene product (protein) or incorrect post-translational modification. Animal cells have often been used as a solution to such problems. Animal cells have the above-mentioned advantages over microbial cells, however, the step of culture of the animal cells is rather complicated, and may result in lowered expression amount of the genes.

To develop a vector for the gene expression in such cells is an important infrastructural issue in many molecular biological studies. Such a vector is required to permit effective mass expression and inducible, transient gene expression, depending on purposes. Conventional ideas on construction of the expression vectors for use in these expression systems that meet the above-mentioned requirements were based on inherent functions of promoters and/or enhancers. Namely, in order to improve efficiency of producing target gene products, the procedure has been extensively practiced in which a strong promoter or enhancer is selected from natural genes and is ligated to a DNA sequence that encodes target proteins or peptides, thereby improving the efficiency of mRNA transcription. For the efficient expression at a higher amount, known strong promoters may include SV40 (Simian Virus 40), SR-α, *cytomegalovirus* promoters, actin promoters, viral LTRs (Long Terminal Repeat) including HTLV-1 LTR, HIV-LTR, and Rous sarcoma virus LTR, and herpes simplex virus tyrosine kinase promoter. Expression vectors with these promoters incorporated therein have been used mainly in mammalian cells. Alternatively, an enhancer sequence has been incorporated into a vector to improve efficiency of gene transcription, which in turn improves efficiency of production of target gene products.

For the transient gene expression, substances that can induce expression have been used, for example, dexamethasone, a substance that can induce expression, has been added when expression is desired in expression systems in which a mouse mammalian tumor virus (MMTV) promoter is used.

On expression from cDNAs (first cistron and second cistron) encoding two different proteins, it has been reported that the two different proteins may be expressed with a single promoter by means of interpositiong a base sequence corresponding to the internal translation initiation signal, between the first and second cistrons (Urabe, M. et al., *Gene,* 200, 157, 1997), which has been applied in practice. However, the expression vectors obtained using such conventional techniques are not necessarily enough to achieve satisfactory production efficiency.

Furthermore, gene therapies that have been developed dramatically in recent years have permitted curative therapy of diseases that are difficult to be achieved with conventional techniques and thus, a wide variety of possible applications have been expected. However, problems to be solved have still remained in order to construct a vector that serves to express target genes at a significantly high efficiency at a specific site in a body of organisms. Specifically, a promoter may achieve less efficient gene expression due to its low activity even if it is organ- or tumor-specific, therefore, transduction of genes by using a vector with such a promoter incorporated therein may not always provide a satisfactory therapeutic effect.

As apparent from the above, it is desired in this technical field to develop an expression vector of which expression efficiency is higher Accordingly, an object of the present invention is to provide a novel expression vector without being bound by any particular theory of vector construction, in order to improve production efficiency of target gene products.

SUMMARY OF THE INVENTION

In order to achieve the above-mentioned object, the present inventors have conducted intensive research and found that expression of a target useful gene is enhanced by means of incorporating a nucleic acid sequence included in a 5'-untranslated region of a viral gene or a fragment or a variant thereof into a gene expression vector. The present invention was thus accomplished.

As used herein, "sequences for enhancing expression of a useful gene" means any sequences comprising a nucleic acid sequence of 5'-untranslated regions or a 5'-untranslated region and a region containing a portion of a coding region adjacent to the 5'-untranslated region, or a fragment or a variant thereof, of any viral genes.

Further, "enhance expression of a useful gene" is used herein to describe consequential enhancement of expression of a useful gene regardless of conditions such as active agents for expression enhancement, process of translation, expression environment, and methods of expression.

In addition, "a portion of a coding region adjacent to the 5'-untranslated region", which may be included in the nucleic acid sequence for enhancing expression of a useful gene according to the present invention, refers to a fragment of bases five times smaller than the 5'-untranslated region, preferably, a fragment having the same number of bases as the 5'-untranslated region or about 100 bases smaller or larger number of bases than the 5'-untranslated region.

Preferably, the 5'-untranslated region in the nucleic acid sequence for enhancing expression of a useful gene comprises at least one pyrimidine-rich tract and, more preferably, it further comprises a sequence corresponding to a region selected from the group consisting of BoxA, BoxB, a trans factor-binding site, and a combination thereof, or an AUG or ATG sequence. The regions and sequences may be preferably incorporated in the nucleic acid sequence for enhancing expression of a useful gene, without any mutation or fragmentation. Such an AUG or ATG sequence as well as an AUG or ATG sequence contained in BoxB may be incorporated, as an initiation codon, into the extreme downstream site of the nucleic acid sequence for enhancing expression of a useful gene or the extreme upstream site of the coding region for example.

Moreover, the 5'-untranslated region in the nucleic acid sequence for enhancing expression of a useful gene preferably comprises a part of or an entire region of viral mRNA IRES. The region of IRES may or may not have IRES activity but it is preferable that the region, from which the IRES has been derived, has IRES activity.

When the 5'-untranslated region in the nucleic acid sequence for enhancing expression of useful genes comprises any sequence corresponding to a pyrimidine-rich tract, BoxA, BoxB and/or trans factor-binding site, those having a substitution, deletion, insertion and/or addition mutation(s) of a single or a few nucleotides of a sequence derived from a wild-type virus within the sequence or a proximate sequence(s) (regions other than highly conserved ones) to the sequence in at least one position among the above, are also preferable as the nucleic acid sequence for enhancing expression of a useful gene according to the present invention. When the nucleic acid sequence for enhancing expression of a useful gene comprises a sequence corresponding to a variable region of the 5'-untranslated region, it is preferable that the corresponding sequence contains a mutation sequence i.e., substitution, deletion, insertion and/or addition of a single or a few nucleotides of a sequence derived from a wild-type virus. It is preferable that the mutation(s) can accelerate directly or indirectly IRES activity.

The nucleic acid sequence for enhancing expression of a useful gene containing the above-mentioned 5'-untranslated region or a variant of a fragment thereof is preferably obtained through mutation including substitution, insertion and/or deletion in a region other than the highly conserved region of the 5'-untranslated region of a viral gene. In particular, when the nucleic acid sequence for enhancing expression of a useful gene includes IRES, the pyrimidine-rich tract, in particular, a variant where BoxA and/or BoxB are/is conserved may advantageously be used. A mutation may be introduced into the sequence by using, for example, a mutagenesis technique using PCR.

The location where the nucleic acid sequence for enhancing expression of a useful gene is incorporated into a gene expression vector should be the one that permit direct or indirect enhancement of expression of a useful gene by means of incorporating the nucleic acid sequence for enhancing expression of a useful gene into an expression vector which has been constructed such that the useful gene can be expressed, however, it is preferable that the location is downstream of the expression regulatory promoter sequence and upstream of the useful gene. Additionally, the nucleic acid sequence for enhancing expression of a first useful gene should be incorporated into the expression vector such that transcription and translation are carried out in the normal (i.e., from 5' to 3') direction.

The nucleic acid sequence for enhancing expression of a useful gene incorporated into the gene expression vector may preferably be a cDNA sequence. Further, the gene expression vector may preferably be a vector for expression in eukaryotic cells.

The virus mentioned above may preferably be an RNA virus such as a *picornavirus* or HCV virus.

For the case of the 5'-untranslated region of HCV mRNA, BoxA is found at the nucleotide positions 191–199 of SEQ ID NO: 1, the pyrimidine-rich tracts located upstream of the BoxA are at the nucleotide positions 40–46 and 120–130 of SEQ ID NO: 1, and BoxB is at the nucleotide positions 213–219 of SEQ ID NO: 1 (See FIG. 1, in which the trans factor-binding sites are encircled), whereas the variable regions are at the nucleotide positions 1–36 and 175–270 of SEQ ID NO: 1, and the highly conserved regions are at the nucleotide positions 121–174 and 271–339 of SEQ ID NO: 1.

Examplary fragment of a nucleic acid sequence of the HCV-derived 5'-untranslated region or the region on the 5'-end side (i.e., 5'-untranslated region and a portion of the coding region adjacent to the untranslated region) to be comprised in the nucleic acid sequence for enhancing expression of a useful gene for incorporation into the gene expression vector, may currently be the nucleic acid sequences including the nucleotide positions 1–180, 181–341, 1–341, 181–713 or 1–713 of SEQ ID NO: 1, which are demonstrated to be preferable. Among these fragments, it has been revealed that a particularly striking activity for enhancement of expression of a useful gene was observed on the fragments including the nucleotide positions 181–341 of SEQ ID NO: 1 (see, Examples 5 and 6).

In addition, it has been revealed that the nucleic acid sequence for enhancing expression of a useful gene that is incorporated into the gene expression vector may particularly preferably comprise the nucleic acid sequence including the nucleotide positions 1–342 of SEQ ID NO: 7 or a nucleic acid sequence having a substitution of the nucleotide position 119 of this sequence with adenine.

When the virus used is HCV, it is preferable that the HCV-derived 5'-untranslated region or a variant of the nucleic acid sequence in the region on the 5'-end side to be comprised in the nucleic acid sequence for enhancing expression of a useful gene may be, among others having preferable mutation(s) described above, a nucleic acid sequence comprising a part of or an entire sequence of SEQ ID NO: 1 and that has one or a few nucleotides inserted at the nucleotide position 207 or in the vicinity thereof, and, more preferably, is a nucleic acid sequence that has one thymidine inserted into that position.

When an HCV-derived nucleic acid sequence is used, the coding region adjacent to the 5'-untranslated region is a core protein, and about 300 bases on the 5' side, of the region encoding the core protein may be included in the nucleic acid sequence for enhancing expression of a useful gene.

Therefore, such a nucleic acid sequence for enhancing expression of a useful gene is also suitable for the present invention that further comprises a portion of the coding region of the core protein of the HCV. Additionally, a variant of the nucleic acid sequence may preferably be the sequence obtained through substitution, insertion and/or deletion mutation(s) in a variable region (regions other than highly conserved ones).

The present invention further contemplates an isolated polynucleotide consisting of nucleotide sequences set out in SEQ ID NO: 7, and a polynucleotide having a similar IRES activity to this nucleic acid sequence and consisting of a fragment or a variant of the sequence (i.e., an HCV-derived nucleic acid sequence of the nucleotide positions 1–341 of SEQ ID NO: 1, wherein at least one base is inserted between the positions 206 and 207, a variant or a fragment thereof). These polynucleotides have a quite higher IRES activity as compared with the HCV-derived IRES sequences known in the art. Therefore, it becomes possible to use this polynucleotide for the production of polypeptides by the conventional expression with a host cell, and to incorporate the polynucleotide into a vector for gene therapy to achieve more efficient initiation of translation. Since the polynucleotide itself has a higher IRES activity than those known in the art, it may be used for curative treatment of diseases resulting from reduction of IRES activity due to, for example, a mutation on the IRES active site in vivo.

Hereinafter, a sequence specifically indicated as "5'-UTR341" means the one including SEQ ID NO: 1 and a fragment thereof, while a sequence specifically indicated as "5'-UTR342" means the one derived from an HCV variant (SEQ ID NO: 7) obtained according to the present invention.

Further, it is preferable that the nucleic acid sequence for enhancing expression of a useful gene is the one (e.g., 5'-UTR341) that enhances expression of a useful gene by means of its own translation promoting activity and the one (e.g., 5'-UTR342) that enhances expression of a useful gene by means of accelerating IRES activity.

The present invention also contemplates a vector for gene expression comprising the above-mentioned nucleic acid sequence for enhancing expression of a useful gene, a host cell transformed or transfected with the vector in question, a method for expressing and producing a useful gene product by using the vector, and a method for enhancing expression of a useful gene by using the vector.

According to another aspect of the present invention, there is provided a probe for screening substances that interact with IRES, comprising an isolated polynucleotide consisting of nucleotide sequences of SEQ ID NO: 7 or a polynucleotide having a similar IRES activity to this nucleic acid sequence and consisting of a fragment or a variant of the sequence (i.e., a sequence wherein at least one base is inserted between the positions 206 and 207 of the nucleotide sequence of HCV 5'-UTR341 (the nucleotide positions 1–341 of SEQ ID NO: 1), a variant or a fragment thereof). The probe is preferably labeled to identify a target substance using its interactivity with IRES. The "substances that interact with IRES" as used herein means those that can change directly or indirectly (by, for example, forming a complex with other factors) IRES activity as well as the substances that bind to IRES. Examplary substances may include IRES-binding proteins, pyrimidine region-binding proteins, trans factors, and translation initiators. Thus, the interacting substances are expected to be modulators that cause inhibition, enhancement or the like of IRES. The probe may be immobilized on a solid support or used in a liquid phase.

The present invention further provides a probe for screening an IRES-dependent translation initiator, comprising an isolated polynucleotide consisting of nucleotide sequences of SEQ ID NO: 7 or a polynucleotide having a similar IRES activity to this nucleic acid sequence and consisting of a fragment or a variant of the sequence (i.e., a sequence wherein at least one base is inserted between the positions 206 and 207 of the nucleotide sequence of HCV 5'-UTR341 (the nucleotide positions 1–341 of SEQ ID NO: 1), a variant or a fragment thereof). The probe is also preferably labeled to identify a target through identifying association with the IRES-dependent translation initiator and effects on the initiation of translation.

To date, it has been revealed that an IRES-dependent mRNA translation initiation mechanism is used in eukaryotic cells by c-myc (Nanbru C. et al., *J Biol.Chem.*, 272 (51), 32061–32066, 1998; Stoneley, M. et al., *Oncogene*, 16 (3), 0.423–428, 1998), BiP (immunoglobulin heavy chain binding protein) (Le S. Y. et al., *Nucleic Acids Res.*, 25 (2), 362–369, 1997; Yang Q. et al, *Nucleic Acids Res.*, 25 (14), 2800–2807, 1997), FGF-2 (Le S. Y. et al., *Nucleic Acids Res.*, 25 (2), 362–369, 1997), PDGF2 (Bernstein J. et al., *J.Biol.Chem.*, 271 (14), 9356–9362, 1997), eIF-4G (Gan W. et al., *J.Biol.Chem.*, 273 (9), 5006–5012, 1998), and potassium channels.

As apparent from Examples described below, the novel 5'-UTR342 sequence was isolated from the serum of a patient suffering from hepatitis C where viruses replicate extensively, therefore, determination of the severity of hepatitis C is allowed by means of distinguishing a difference in sequence from 5'-UTR341. In particular, the present invention contemplates a method for determining the severity of hepatitis C, comprising: detecting the presence of the polynucleotide sequence contained in a biological sample derived from a test subject, by using, as a target, an isolated polynucleotide consisting of nucleotide sequences of SEQ ID NO: 7 or a polynucleotide having a similar IRES activity to this nucleic acid sequence and consisting of a fragment or a variant of the sequence (i.e., a sequence wherein at least one base is inserted between the positions 206 and 207 of the nucleotide sequence of HCV 5'-UTR341 (the nucleotide positions 1–341 of SEQ ID NO: 1), a variant or a fragment thereof) to determine the severity of the hepatitis C based on the presence of the sequence.

Finally, the present invention provides a therapeutic composition for treating diseases resulting from reduction of cap-dependent mRNA translation or diseases resulting from reduction of IRES activity, in a body of organisms, comprising a nucleic acid sequence for enhancing expression of a useful gene such that translation of mRNA can be promoted by means of introducing the nucleic acid sequence for enhancing expression of a useful gene into the body the organisms. Curative or prophylactic therapy of the diseases can be accomplished by introducing these sequences to compensate a compromised mRNA translation mechanism.

More specifically, the present inventors have found that, when the nucleic acid sequence for enhancing expression of a useful gene is incorporated between the promoter sequence and the cDNA sequence encoding luciferase protein within the vector, luciferase exhibits a higher enzymatic activity compared with a case where conventional vectors are expressed without such a nucleic acid sequence. The increase in an amount of enzymatic protein is expected to be responsible for the accelerated activity, therefore, it has been shown that the incorporated sequences achieve an effect of enhancing expression of a useful gene.

Additionally, such effects can be observed for other promoters and luciferase originated from different sources, therefore, it has been revealed that this phenomenon may be relatively common rather than occurring with a particular combination of a specified promoter sequence, a nucleic acid sequence for enhancing expression of a useful gene, and a specified useful gene sequence. Moreover, upon identification of the region having the above-mentioned effect with varied nucleic acid sequence for enhancing expression of a useful gene in chain length, consequently, it was found that a stretch of the nucleotide positions 181–341 (SEQ ID NO: 1) on the 5' side of HCV (e.g., HCV JTB strain and the like) genes exhibits a strong effect. In addition, it was also found that the sequence of SEQ ID NO: 7 obtained from a clinical isolate which is a variant strain of HCV1b, or a sequence having a substitution of the nucleotide position 119 of the sequence with adenine may particularly be suitable for the function of enhancing the gene expression. In particular, when the nucleic acid sequence for enhancing expression of a useful gene according to the present invention is used for IRES activity-dependent translation, 5'-UTR342 can be advantageously used, on the other hand, when the nucleic acid sequence for enhancing expression of a useful gene according to the present invention is used for IRES activity-independent translation (e.g., cap-dependent translation and the like), 5'-UTR341 and 5'-UTR342 can be advantageously used. These effects can be applied for the purpose of increasing in vitro the production of proteins or peptides (e.g., cytokine and the like) in a simple cell culture system as well as to vectors for gene therapies effective also in vivo, in combination with such a promoter that is specific to an internal organ or a tumor but has been found difficulties to come into practical use due to its low activity.

Examples of useful genes of the present invention may include nucleic acids encoding peptides which can be expressed in a host, nucleic acids encoding a decoy which comprises a gene encoding a binding protein of a cell-derived transcriptional regulation factor or a sequence of a binding site of a transcriptional regulation factor or an analogous sequence, and suicide genes. The gene is preferably a genomic DNA, cDNA, or partially or entirely chemically synthesized DNA, and more preferably cDNA.

The peptides may include oligopeptides, polypeptides, and proteins, whereas the peptides of the present invention encompass those subjected to modification by sugar, lipid, phosphoric acid, or metal after transcription and translation of the genes. Examplary peptides may include, but are not limited to, useful peptides, for example, insulin, several kinds of interferons, erythropoietin, mannan-binding protein, conglutinin, neurosin, and the like.

The above-described nucleic acids encoding a decoy represent those encoding a binding protein of a cell-derived transcriptional regulation factor or those comprising a sequence of a binding protein of a cell-derived transcriptional regulation factor or a sequence of a binding site of a transcriptional regulator or an analogous sequence thereof. Introduction of these nucleic acids into cells as a decoy may possibly inhibit binding of the transcriptional regulation factor to the binding site, then inhibit effects of the transcriptional regulation factor, and eventually suppress gene clusters to be activated.

The suicide genes may be genes including, for example, an apoptosis-inducing gene (programmed cell death-inducing gene) and a necrosis-inducing gene, the expression of which consequently results in cell death.

Moreover, the useful gene may be expressed as a fusion protein. Fusion proteins may be those expressed from the useful gene in which an N-terminus peptide chain derived from another protein is added to their N-terminus, or in which a suitable peptide chain is added to their C-terminus.

The nucleic acids which can be used for obtaining the nucleic acid sequence for enhancing expression of a useful gene according to the present invention may be derived from any sources having an untranslated region at the 5'-end of their gene (preferably mRNA). In particular, those comprising a part of or an entire region of IRES in the 5'-untranslated region of their mRNA are preferable.

Described in detail below are viruses having a sequence that can be applied as the nucleic acid sequence for use in enhancing expression of a useful gene in the present invention.

Viruses contain either RNA or DNA as genetic material, in the virus particle, and are generally classified into DNA viruses and RNA viruses.

The DNA viruses are generally classified into the following groups:

(1) double-stranded DNA viruses which proliferate within the nuclei, for example, Papovaviridae, Adenoviridae, and *Herpesviridae;*

(2) double-stranded DNA viruses which proliferate within the cytoplasm, for example, Poxyviridae;

(3) single-stranded DNA viruses which proliferate within the nuclei, for example, Parvoviridae;

(4) *Iridoviruses*, for example, Iridoviridae; and (5) *Hepadnaviruses*, for example, Hepadnaviridae.

On the other hand, the RNA viruses are generally classified into the following groups:

(1) plus single-stranded RNA viruses, for example, Picornaviridae, Togaviridae, Flaviviridae, Caliciviridae, and Coronaviridae;

(2) non-segmented, minus single-stranded RNA viruses, for example, Paramyxoviridae, Rhabdoviridae, and Filoviridae;

(3) segmented, minus single-stranded RNA viruses, for example, Orthomyxoviridae, Bunyaviridae, and Arenaviridae;

(4) double-stranded RNA viruses, for example, Reoviridae;

(5) ambisense RNA viruses, for example, Arenaviridae and Bunyaviridae; and (6) *retroviruses*, for example, Retroviridae.

The family, generic, and species name of the representative DNA and RNA viruses having a 5'-untranslated region in the gene are presented below, and the nucleic acid sequence for enhancing expression of a useful gene according to the present invention may be selected from the sequences derived from these viruses, alternatively, may be selected from the sequences derived from a variant thereof or from a novel species, in addition, may be selected from those derived from other DNA or RNA viruses except for the above viruses.

Typical genera of the family Papovaviridae may include *Papillomavirus*, Polyoma virus, and the like, wherein typical species may include Shope papilloma virus, polyoma virus, vacuolating virus, and the like.

Typical genera of the family Adenoviridae may include *Mastadenovirus, Aviadenovirus*, and the like, wherein typical species may include human adenovirus, CELO virus, and the like.

Typical genera of the family Herpesviridae may include *Alphaherpesvirus, Betaherpesvirus, Gammaherpesvirus*, and the like, wherein typical species may include herpes simplex virus type I, herpes simplex virus type II, varicella-zoster virus, B virus, cytomegalovirus, EB virus, HHV-6, HHV-7, and the like.

Typical genera of the family Poxviridae may include *Orthopoxvirus, Avipoxvirus, Capripoxvirus, Leporipoxvirus, Parapoxvirus, Suipoxvirus, Entomopoxvirus, Yatapoxvirus, Molluscipoxvirus*, and the like, wherein typical species may include vaccinia virus, fowlpox virus, sheeppox virus, *myxomavirus*, orf virus, swinepox virus, insectpox viruses, Yata virus, molluscum contagiosum virus, and the like.

Typical genera of the family Parvoviridae may include *Parvovirus, Dependovirus*, and *Densovirus*, and the like, wherein typical species may include parvovirus B19, adeno-associated satellite virus, densonucleosis virus, and the like.

Typical genera of the family Iridoviridae may include *Iridovirus*, and the like, wherein typical species may include iridescent virus, and the like.

Typical genera of the family Hepadnaviridae may include *Hepadnavirus*, and the like, wherein typical species may include hepatitis B virus, and the like.

Typical genera of the family Picornaviridae may include *Enterovirus, Heparnavirus, Rhinovirus*, and the like, wherein typical species may include *poliovirus* type I, *poliovirus* type III (*polyovirus* type I), coxsackie A and B viruses (except for serotypes 1–5), hepatitis A virus, *echovirus*, human rhinovirus type 1A, *enterovirus*, and the like.

Typical genera of the family Togaviridae may include *Alphavirus, Rubivirus, Pestivirus*, and the like, wherein typical species may include sindbis virus, rubella virus, Eastern equine encephalomyelitis virus, bovine mucosal disease virus, and the like.

Typical genera of the family Flaviviridae may include *Flavivirus, Hepacavirus*, and the like, wherein typical species may include Japanese B encephalitis virus, yellow fever virus, hepatitis C virus, and the like.

Typical genera of the family Caliciviridae may include *Calicivirus, Hepevirus*, and the like, wherein typical species may include Norwalk virus, hepatitis E virus, and the like.

Typical genera of the family Coronaviridae may include *Coronavirus*, and the like, wherein typical species may include human *coronavirus*, avian infectious bronchitis virus, mouse hepatitis virus, and the like.

Typical genera of the family Paramyxoviridae may include *Pneumovirus, Paramyxovirus, Morbillivirus*, and the like, wherein typical species may include respiratory syncytial virus, newcastle disease virus, measles virus, mumps virus, para influenza virus, and the like.

Typical genera of the family Rhabdoviridae may include *Vesiculovirus Lyssavirus*, and the like, wherein typical species may include vesicular stomatitis virus, rabies virus, and the like.

Typical genera of the family Filoviridae may include *Filovirus*, and the like, wherein typical species may include Marburg virus, Ebola virus, and the like.

Typical genera of the family Orthomyxoviridae may include *Influenzavirus*, and the like, wherein typical species may include influenza viruses type A, B and C, swine influenza, and the like.

Typical genera of the family Bunyaviridae may include *Bunyavirus*, and the like, wherein typical species may include Bunyawera virus, Hantaan virus, Crimean-Congo hemorrhagic virus, and the like.

Typical genera of the family Arenaviridae may include *Arenavirus*, and the like, wherein typical species may include lymphocytic chorimengitis virus, Lassa virus, and the like.

Typical genera of the family Reoviridae may include *Orbivirus, Reovirus, Rotavirus*, and the like, wherein typical species may include bluetongue virus, human reovirus, rotavirus, and the like.

Typical subfamilies of the family Reoviridae may include Oncovirinae, Spumavirinae, Lentivivirinae, and the like, wherein typical species may include human T cell leukemia virus, human immunodeficiency virus, and the like.

The nucleic acid sequence for enhancing expression of a useful gene, which may be used in the present invention, may be a 5'-untranslated region present in the nucleic acid sequence of all viruses including the aforementioned DNA and RNA viruses or a sequence that comprises a stretch of the nucleic acid sequence expanding from the untranslated region to the adjacent coding region, or a fragment thereof, or a variant of these sequences. The 5'-untranslated region means the regions located at the 5'-end and which are not translated into amino acid sequence, moreover, as the nucleic acid sequence for enhancing expression of a useful gene, the region may or may not have IRES activity, although it preferably has such activity. The 5'-untranslated region may includes 5'-UTR (5'-untranslated region or 5-untranslating region) and 5'-NCR (5'-noncoding region), 5'-NTR (5'-nontranslated region), and the like.

A method for obtaining the nucleic acid sequence for enhancing expression of a useful gene from the above-mentioned viruses is described below. Double-stranded DNA viruses that proliferate within the nuclei contain a double-stranded DNA (dsDNA) as the genome, thus, mRNA can be synthesized from dsDNA by the DNA-dependent RNA polymerase II to prepare a sequence comprising a sequence of the 5'-untranslated region of the nucleic acid sequence or a sequence that comprises a stretch of the nucleic acid sequence expanding from the untranslated region to the adjacent coding region, or a fragment thereof. Besides, double-stranded DNA viruses that proliferate within the cytoplasm contain a dsDNA as the genome, therefore, mRNA can be synthesized by the DNA-dependent RNA polymerase that is inherent to the virus to use the sequence comprising a sequence of the 5'-untranslated region of the nucleic acid sequence or a sequence that comprises a stretch of the nucleic acid sequence expanding from the untranslated region to the adjacent coding region, or a fragment thereof. Single-stranded DNA viruses that proliferate within the nuclei have a single-stranded DNA (ssDNA) as the genome, therefore, it is possible to synthesize dsDNA by the DNA polymerase followed by mRNA synthesis by the DNA-dependent RNA polymerase II to use a sequence comprising a sequence of the 5'-untranslated region of the resulted nucleic acid or a sequence that comprises a stretch of the nucleic acid sequence expanding from the untranslated region to the adjacent coding region, or a fragment thereof. *Hepadnaviruses* contain a partially double-stranded circular DNA as the genome, therefore, a gap is repaired and then DNA is supercoiled, thereafter, the supercoiled DNA is used to synthesize mRNA by the DNA-dependent RNA polymerase II. Thus, a sequence comprising the 5'-untranslated region of the resulted nucleic acid sequence or a sequence that comprises a stretch of the nucleic acid sequence expanding from the untranslated region to the adjacent coding region, or a fragment thereof can be used.

A method for obtaining the nucleic acid sequence for enhancing expression of a useful gene from RNA viruses is described below. Plus strand RNA viruses contain an mRNA as the genome, therefore, a sequence comprising the 5'-untranslated region of the nucleic acid sequence or a sequence that comprises a stretch of the nucleic acid sequence expanding from the untranslated region to the adjacent coding region, or a fragment thereof can be used. For non-segmented and segmented, minus strand RNA viruses, it can be converted to complementary plus strand RNA by the ssRNA-dependent RNA polymerase (replicase to use a sequence comprising the 5'-untranslated region of the nucleic acid sequence or a sequence that comprises a stretch of the nucleic acid sequence expanding from the untranslated region to the adjacent coding region, or a fragment thereof. Double-stranded RNA viruses contain a segmented dsRNA as the genome, therefore, mRNA can be synthesized by the dsRNA-dependent RNA polymerase to use a sequence comprising the 5'-untranslated region of the sequence or a sequence that comprises a stretch of the nucleic acid sequence expanding from the untranslated region to the adjacent coding region, or a fragment thereof. Ambisense RNA viruses contain both plus and minus strand as the genomes, therefore, mRNA can be synthesized by the ssRNA-dependent RNA polymerase to use a sequence comprising the 5'-untranslated region of the nucleic acid sequence or a sequence that comprises a stretch of the nucleic acid sequence expanding from the untranslated region to the adjacent coding region, or a fragment thereof. For retroviruses, a DNA-RNA hybrid can be formed by RNA-dependent DNA polymerase (reverse transcriptase) using a tRNA primer, thereafter, the RNA hybridized to DNA can be is separated by means of the ribonuclease H(RNase) H activity of the reverse transcriptase to synthesize a linear dsDNA. After adequate treatment of the linear dsDNA, mRNA can be synthesized by the DNA-dependent RNA polymerase II to use a sequence comprising the 5'-untranslated region of the nucleic acid sequence or a sequence that comprises a stretch of the nucleic acid sequence expanding from the untranslated region to the adjacent coding region, or a fragment thereof.

When a cDNA sequence is used as the nucleic acid sequence for enhancing expression of a useful gene according to the present invention, it is preferable that such cDNA is prepared from mRNA obtained in the manner described above, using the reverse transcriptase. Besides, other suitable DNAs may include genomic DNA sequences prepared from a virus genome by using, for example, PCR and the like, and DNAs partially or entirely chemically synthesized by using, for example, a DNA synthesizer based on the information obtained by nucleotide sequencing.

The expression vector according to the present invention may be constructed to allow expression of a useful gene both in vitro and in vivo, and is not particularly limited, which may be any one in which the nucleic acid sequence for enhancing expression of a useful gene according to the present invention is ligated to a location preferably downstream of the promoter sequence and upstream of the useful gene. Vectors used for construction of the expression vector may be commercially available ones. Such vectors may include, for example, pUC19 and pTV118N (Takara Shuzo Co., Ltd.), pUEX2 (Amersham), pGEX4T and pKK233-2 (Pharmacia), pMAM-neo (Clontech), pGL2 (Promega), pDNA3.1+(Invitrogen), and the like. The expression vector of the present invention may be constructed by any one of standard techniques such as those using restriction enzymes or ligase.

The "expression vector" used herein is not limited to the vectors used in Examples, instead, the vector may be a replicon, such as plasmid, λ-phage or cosmid, in which the nucleic acid sequence having activity to enhance expression of the useful gene are incorporated so that the replication and expression of the useful gene may be effected. For example, examplary expression vectors that can clone longer DNA fragments than those cloned using cosmid, may include P1 phage, F factors, Yeast Artificial Chromosome (YAC), and the like. The λ-phage may include a substitution vector and an insertion vector, either of which may be selected adequately depending on the length of the useful gene.

Examples of known vectors that can be expressed in animal cells may include SV40 vectors, bovine *papillomavirus* vectors, *herpesvirus* vectors, *adenovirus* vectors, *poxvirus* vectors, *retrovirus* vectors, and the like.

When a bacteria, especially *Escherichia coli*, is used for the host cell into which the expression vector is transformed or transfected, the expression vector typically comprises at least a promoter region (including promoter, operator and Shine-Dalgarno sequences), an initiation codon, a useful gene sequence, a termination codon, and a terminator region. When the host used is yeast or animal cells, the expression vector preferably comprises at least a promoter, an initiation codon, a signal peptide, a useful gene sequence and a termination codon. Furthermore, an enhancer sequence, 5'- and 3'-untranslated regions of the useful gene, a splicing junction, polyadenylation site and a selectable marker may be inserted into the expression vector.

The promoter incorporated into the gene expression vector of the present invention may be either a strong or weak promoter well known in the art, which may include SV40 (Simian Virus 40), SR-α, *cytomegalovirus* (CMV) promoter, actin promoter, viral LTR (Long Terminal Repeat) including HTLV-1 LTR and HIV-LTR, Rous sarcoma virus LTR, herpes simplex virus tyrosine kinase promoter, and the like.

When expression is expected in various kinds of eukaryotic cells including normal cells such as fibroblasts, neurons, blood cells and parenchymal cells as well as carcinoma cells, typical promoters may be *cytomegalovirus* promoter, thymidine kinase (TK) promoter, β-actin promoter, SV40 early gene promoter, and the like. Enhancers are usually combined with promoter sequences and can thus be used as they are.

In general, promoters, which can serve high expression of the useful gene in the cells derived from mammalian animals, may advantageously be selected as the promoter of the present invention as long as they are compatible with the host. In addition, when the cell and tissue where genes are introduced and expressed is specifically determined, a promoter specific to the cell may be selected. Further, the promoters may be combined in a homologous or heterologous manner, thereby a yet higher expression and stabilized expression of the proteins may be expected.

Meanwhile, examples of promoters for prokaryotic cells may include PBAD, PL, trc, T7, SP6, T3, 1ac, and the like.

In general, promoters, which can serve high expression of the useful gene in the cells derived from prokaryotic cells, may advantageously be selected as the promoter of the present invention as long as they are compatible with the host. In addition, when the cell and tissue where genes are introduced and expressed is specifically determined, a promoter specific to the cell may be selected. Further, the promoters may be combined in a homologous or heterologous manner, thereby a yet higher expression and stabilized expression of the proteins may be expected.

Examplary promoters for yeast may include GAL1, AOX1, CUP1, PGK, and the like.

Selectable markers to be incorporated into the gene expression vector for selection of cells expressing the target vector may be dihydrofolate reductase (DHFR) genes (methotrexate-resistant genes), neo genes (G418-resistant genes), or the like. For example, when a DHFR gene is used as a selective marker for a CHO cell lacking DHFR genes, selection may be conducted using a thymidine-free culture medium. Alternatively, cell lines with higher expression can be obtained through culture with increased concentration of methotrexate to select resistant cells, resulting in intracellular expression of the useful gene.

Examples of the expression vectors constructed are schematically illustrated in FIGS. 2–4, 7, 8, 11 and 12 (see, Examples 2–6 and 8–12).

The present invention also contemplates host cells transformed or transfected with the gene expression vectors constructed in the manner described above, such as animal cells, plant cells, insect cells and microbial cells (e.g., *Escherichia coli, Bacillus subtilis, Saccharomyces cerevisiae*, or the like), which can express the useful gene incorporated into the expression vector. Selected as a suitable host cell may be one that can result in maximal activity of the nucleic acid sequence for enhancing expression of a useful gene incorporated between the promoter sequence and the useful gene.

The animal cells used for the host cell according to the present invention may include, for example, those derived from human cells but are not specifically limited as long as the animal cell permits the nucleic acid sequence having activity of enhancing expression of the useful gene used in the present invention to enhance expression of the useful gene therein. Examplary cells may include, for example, CHO cells, COS cells, BHK cells, Vero cells, myeloma cells, HEK293 cells, HeLa cells, Jurkat cells, mouse L cells, mouse C127 cells, mouse FM3A cells, mouse fibroblasts, osteoblasts, chondrocytes, and the like. Besides, examples of microbial cells may include bacteria such as *Escherichia coli* and *Bacillus subtilis* as well as yeasts such as yeast *Saccharomyces cerevisiae* and *Saccharomyces uvarum*. Moreover, plant cells may include cells from a cotton plant and *Arabidopsis*.

As described above, the nucleic acid sequence for enhancing expression of a useful gene preferably has IRES activity, however, viral IRESs may be structurally versatile and may vary in respect to the requirement of the host cells involved in their functions in expression. In addition, some IRES-related molecule clusters may alter their localization upon viral infection, therefore, it is preferable to choose the host adequately, depending on the nucleic acid sequence when the nucleic acid comprising IRES is employed in the present invention.

Moreover, when no suitable host cell can be obtained that permits desirable enhancement of expression, the host cell used may be modified by means of, for example, transformation, and the like. As the procedure for the modification of the host cell, introduction of a trans factor (e.g., La, p25, PTB, and the like) into the host cell, alternatively, transformation of the host cell to allow expression within the host cell, may be carried out. Many molecules involved in the cap-dependent translation initiation are mobilized for the expression of IRES functions, as well as other trans factors. The term "trans factor" used herein means a cluster of molecules derived from the host cell that can impart or accelerate, directly or indirectly, the activity of enhancing expression of the useful gene of the present invention. As set forth above, the conformation of RNAs as well as the trans factors that act on IRES play important roles in the initiation of translation, however, the trans factors required may be different depending on each IRES, and a mechanism leading to functional expression are expected to depend on the respective IRES.

Methods for introduction of the expression vector into the host cell may include, for example, transfection by means of lipopolyamine-mediated method, DEAE-dextran method, Hanahan method, lipofectin-mediated method, potassium phosphate-mediated method, as well as the methods of microinjection, electroporation, and the like.

A promoter having affinity with prokaryotic RNA polymerase to be used in eukaryotic cells, and an IRES-dependent translation mechanism may be both applied to practice the present invention through performing a certain treatment. For example, as described in Examples of the present invention, the useful gene may be expressed in the eukaryotic cytoplasm using a host cell into which polymerase genes that are compatible with the promoter have been previously introduced. Methods for the introduction may include any conventional method, for example, a method in which a liposome preparation employing viral envelopes is used, electroporation method, potassium phosphate-mediated method and a method in which a viral vector is employed. In particular, it is useful in the clinical application to use liposome preparations such as HVJ liposome, VSV liposome, cationic liposome, and the like, or viral vectors such as adenovirus vectors, retrovirus vectors, and the like. The liposome preparation or the viral vector may be introduced in an organ- or site-specific manner into eukaryotic cells so that prokaryotic RNA polymerase is expressed, thereafter, the useful gene may be expressed with the expression vector in which the promoter having affinity with the prokaryotic RNA polymerase is used, to allow the organ- or site-specific expression of the useful gene. This approach may provide advantages such as the reduction of possible side effects and the improvement of organ-specificity, even when the liposome preparation or the virus vector is introduced into an undesirable site, because the useful gene can not be expressed in the cells where the promoter-specific polymerase has not been expressed. A sequence of 5'-UTR342 derived from variant HCV provides, in such a case, a higher efficiency of useful gene expression than a sequence of 5'-UTR341 derived from wild-type HCV, as demonstrated in Examples 9–12 (described below).

As described above, the nucleic acid sequence for enhancing expression of a useful gene of the present invention can eventually enhance expression of the useful genes regardless of particular promoters, hosts, causes of effects, difference in translation processes, expression environments, and methods of expression.

Furthermore, the present specification discloses organisms (e.g., animals, plants, and insects) that comprise host cells transformed or transfected with the expression vector comprising the nucleic acid sequence for enhancing gene expression, which efficiently express the useful gene products.

Moreover, the present invention also contemplates a method for producing a useful gene product by growing the host cell in a medium and isolating a useful gene product; or by producing the target gene product in a body of organisms having such a host cell, as well as a method for expressing the useful gene, and a method for enhancing expression of a gene by using the expression vector.

As a modified embodiment of the present invention, a method for searching for and discovering a nucleic acid sequence having a novel 5'-untranslated region and/or IRES may be encompassed, accordingly, the sequence, or a fragment thereof, or a sequence having a span from a 5'-untranslated region to a coding region, or a fragment thereof, or a variant thereof, which are obtained through this method may also be used as the nucleic acid sequence for enhancing expression of a useful gene.

An examplary method for searching for and discovering the nucleic acid sequence having a novel 5'-untranslated region and/or IRES is described below. A subunit of eIF-4F (a complex of eIF4E, eIF-4A and eIF-4γ), that is, eIF-4γ (p220) is known to be cleaved within *poliovirus*-infected cells. Therefore, eIF-4F levels are lowered in the infected cells. Such a condition may be created by means of heat shock. Thus, dephosphorylation of cap-binding protein eIF-4E occurs, accompanied by deterioration of the affinity to the cap structure (Lamphear, B. J. et al., *J. Biol. Chem.*, 266, 2789, 1991). Under such states, translation of mRNAs of which requirement for eIF-4F is high may be inhibited, therefore, only mRNAs of which requirement therefor is low or mRNAs having IRES can be translated. According to the findings described above, it is possible to discover a nucleic acid sequence having IRES (analogous) activity by using heat shock, and the like. In fact, mRNAs which can exert their function even within *poliovirus*-infected cells were searched for, and the IRES comprised in their sequence has been identified (Macejak, D. G. et al., *Nature*, 353, 90, 1991). As another examples, a sequence bank of genes may be searched for a nucleic acid sequence having a long 5'-untranslated region in which a plurality of AUG codons are found. In fact, it has been revealed that a lot of mRNAs involved in development and differentiation of *Drosophila melanogaster* contain many of such sequences, whilst IRESs have been identified on two mRNAs transcribed from *Antennapedia* gene (Antp) (Oh, S. K. et al., *Genes Dev.*, 6, 1643, 1992). It has been speculated that, in the animal cells during their development and differentiation stages, as in the cells subjected to heat shock, phosphorylation of eIF-4E is insufficient and the cap-dependent translation mechanism can not function (Bonneau, A. M. et al, *J. Biol. Chem.*, 262, 11134, 1987).

Furthermore, as described above, it has been reported that regions having IRES activities are found in the 5'-untranslated regions of eukaryotic mRNA, such as c-myc, immunoglobulin heavy chain binding protein (BiP), FGF-2, PDGF2, eIF-4G, potassium channels, and the like, and also, it has been shown that translation is actually initiated by the cap-dependent mechanism in eukaryotic cells.

In addition, mRNA having two cistrons may be used to identify IRES elements. This method is based on the fact that translation of the second cistron having the IRES is conducted even under the conditions where translation of the first cistron is inhibited. In recent years, it has been shown that circular RNAs comprising the IRES of encephalomyocarditis virus (EMCV) direct ribosome binding, even under such conditions where an elongation reaction upon translation is inhibited by sparsomycin (Chen, C. et al, *Science*, 268, 415, 1995).

BRIEF DESCRIPTION OF THE DRAWINGS

FIG. 5 shows compared nucleic acid sequences of two different HCV 5'-untranslated regions (HCV1-341:5'-UTR$_{341}$ (SEQ ID NO: 1, nucleotides 1–341) and HCV-342:5'-UTR$_{342}$ (SEQ. ID NO: 7)

BEST EMBODIMENT FOR CARRYING OUT THE INVENTION

Figure 1:
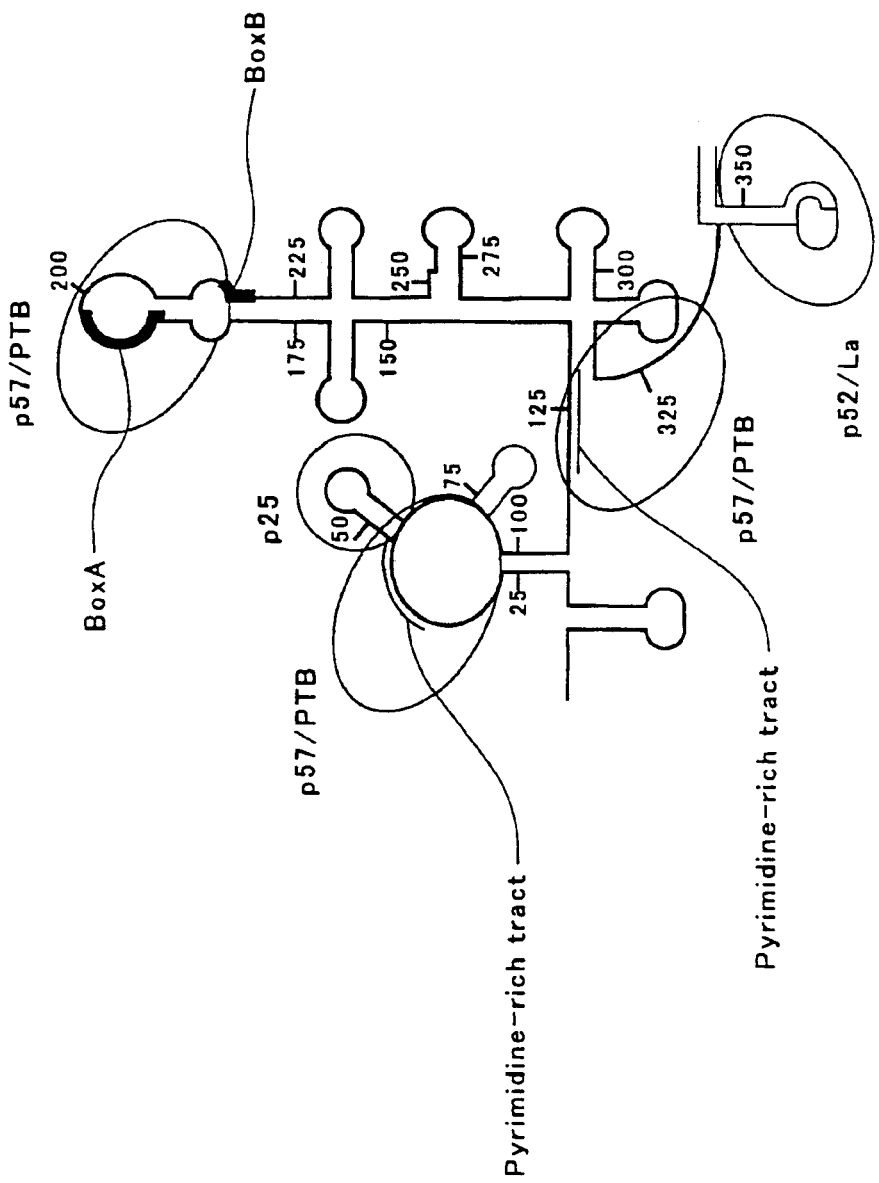
FIG. 1 is a schematic drawing of the secondary structure of an HCV gene in the 5'-untranslated region.

While the present invention is further described with reference to specific embodiments thereof, however, these illustrative embodiments should not be construed as a limitation of the scope of the present invention, and various improvements and modifications on these embodiments which may occur to those skilled in the art are thus contemplated within the scope of the present invention.

In the following embodiment, the procedure of transfecting an expression vector comprising the nucleic acid sequence for enhancing expression of a useful gene according to the present invention into the host cells, and identification of transfectants (assay for luciferase activity) are briefly described first.

[Transfection]

Transfection of expression vectors into host cells in Examples 2–6 described below was performed by a calcium phosphate precipitation method using Profection Mammalian Transfection Systems kit (Promega). Different cell lines were used for these Examples, however in any case, the cells were seeded on one day before transfection, into individual wells (35 mm in diameter) of a 6-well plate such that the cell concentration reached about 50% of the well when used on the next day. More specifically, the cells were seeded into a culture medium of 3 mL at 5×10$^5$ cells and were incubated overnight at 37° C., and 5% CO$_2$. On the day of transfection, the nutrient medium supernatant of the culture cells was aspirated and fresh medium was added to the cell culture before the addition of precipitates of calcium phosphate and expression vector DNAs. The medium that was commonly used in all experiments was Dulbecco's Modified Eagle Medium (DMEM) (GIBCO) supplemented with 10% fetal calf serum.

The precipitates of calcium phosphate and expression vector DNAs were generated as follows. Two polystyrene tubes (A and B) were provided, and then the liquid contained in the kit, CaCl$_2$ and the expression vector DNAs were mixed in the tube A, while the same volume of 2×HEPES (50 mM HEPES, (pH 7.1), 280 mM NaCl, 1.5 mM Na$_2$HPO$_4$) contained in the kit as the mixture in the tube A was placed into the tube B. The solution in the tube A was slowly, and completely added dropwise to the tube B while stirring, which was allowed to stand for 30 minutes at room temperature, to yield slightly clouded solution. After thus resulted liquid was thoroughly mixed with a vortex mixer, the mixture in the tube was then completely added dropwise to the cell culture liquid in a single well such that 5 µg of DNAs were loaded into the well. Subsequently, the nutrient medium was aspirated after incubation at 37° C. for 6 hours and the surface of the cells was washed twice with PBS (−) (phosphate buffered saline (pH 7.4): 137 mM NaCl, 8.10 mM Na$_2$BPO$_4$ (anhydride), 2.68 mM KCl, 1.47 mM KH$_2$PO$_4$) The fresh medium was then added thereto, followed by further culture at 37° C. for 48 hours.

[Assay Method for Luciferase Activity]

Luciferase activity was assayed with the Luciferase Assay System (Promega) in Examples 2, 3, 4, 10, and 12 where the pGL2 vector was used, or with the Dual Luciferase Assay System (tradename; Promega) in Examples 5, 6, 9, 10, and 12 where other vectors were used. At 48 hours after the transfection was performed in the manner described above, lysis buffer contained in the kit was added to each well at 500 µl/well and the luciferase in the cells were extracted according to the manufacturer's instructions in order to obtain a luciferase enzyme solution from the cells in each of the wells.

The luciferase activity was measured for the enzyme solution thus obtained. In particular, using Luciferase Assay System (Promega; in Examples 2, 3, 4, 10, and 12) or Dual Luciferase Assay System (Promega; in Examples 5, 6, 9, 10, and 12), 20 µl of enzyme solution, 100 µl of Luciferase Assay Reagent was added, thereafter, each of the samples was determined for 1 minute at room temperature with the Luminesence Reader BRL-301 (Aloka) according to the manufacturer's instructions.

Protein contents in the remaining enzyme solution after the measurement of luciferase activities were determined using the Coomassie Plus Protein Assay Reagent (PIERCE) with attached bovine serum albumin standard solution in order to represent the luciferase activities in the values per weight of protein in the enzyme solution.

In Examples 2 to 6, respective experiments were carried out in double or triple experiments, starting form the transfection experiments. Specifically, a kind of DNA was independently transfected into host cells at two or three wells respectively, and luciferase activities of the respective enzyme solutions from the wells were measured. It should be noted that the data listed in the Tables 1–5 below are not the results obtained by measuring 2 to 3 times the activities of the enzyme solution from the identical transfectant.

Example 1

Preparation of Fragments of Nucleic Acid Sequence of HCV

As the nucleic acid sequence for enhancing expression of a useful gene, cDNA sequences comprising the regions of MS derived from the 5'-untranslated region of HCV were prepared. After extracting mRNA from the serum of HCV patients according to the standard technique, and cDNA was synthesized through a reaction by reverse transcriptase (GIBCO BRL). Using this cDNA as a template, PCR was performed using the primers of the following sequences (having a HindIII recognition site added at the 5'-end; SEQ ID NOs: 2–6) in order to amplify particular fragments having IRES activity which include the HCV 5'-untranslated region (SEQ ID NO: 1; the nucleotide positions 1–341) and a portion of the core protein coding region (SEQ ID NO: 1; the nucleotide positions 342–713):

5'HindHCV001: 5'-ccc aag ctt gcc agc ccc ctg atg ggg gcg a-3' (SEQ ID NO: 2)

5'HindHCV180: 5'-ccc aag ctt ctg gca att ccg gtg tac tca c-3'(SEQ ID NO: 3)

5'HindHCV181: 5'-ccc aag ctt gac gac cgg gtc ctt tct tg-3'(SEQ ID NO: 4)

3'HindHCV341: 5'-cct aag ctt ggt gca cgg tct acg aga cct-3' (SEQ ID NO: 5)

3'HindHCV713: 5'-cc aag ctt atc gat gac ctt acc ca-3'(SEQ ID NO: 6)

PCR was performed with 20 cycles of. 30 seconds at 94° C.; 30 seconds at 55° C. and 30 seconds at 72° C. Thus, fragments including the HCV 5'-untranslated region, that is, the DNA fragments having a sequence as following nucleotide positions of SEQ ID NO: 1: 1–180, 181–341, 1–341, 1811–713, and 1–713 of SEQ ID NO: 1 were obtained. These fragments are hereinafter referred to as HCV1–180, HCV181–341, HCV1–341, HCV181–713 and HCV 1–713.

Example 2

Transient Transfection

Figure 2:
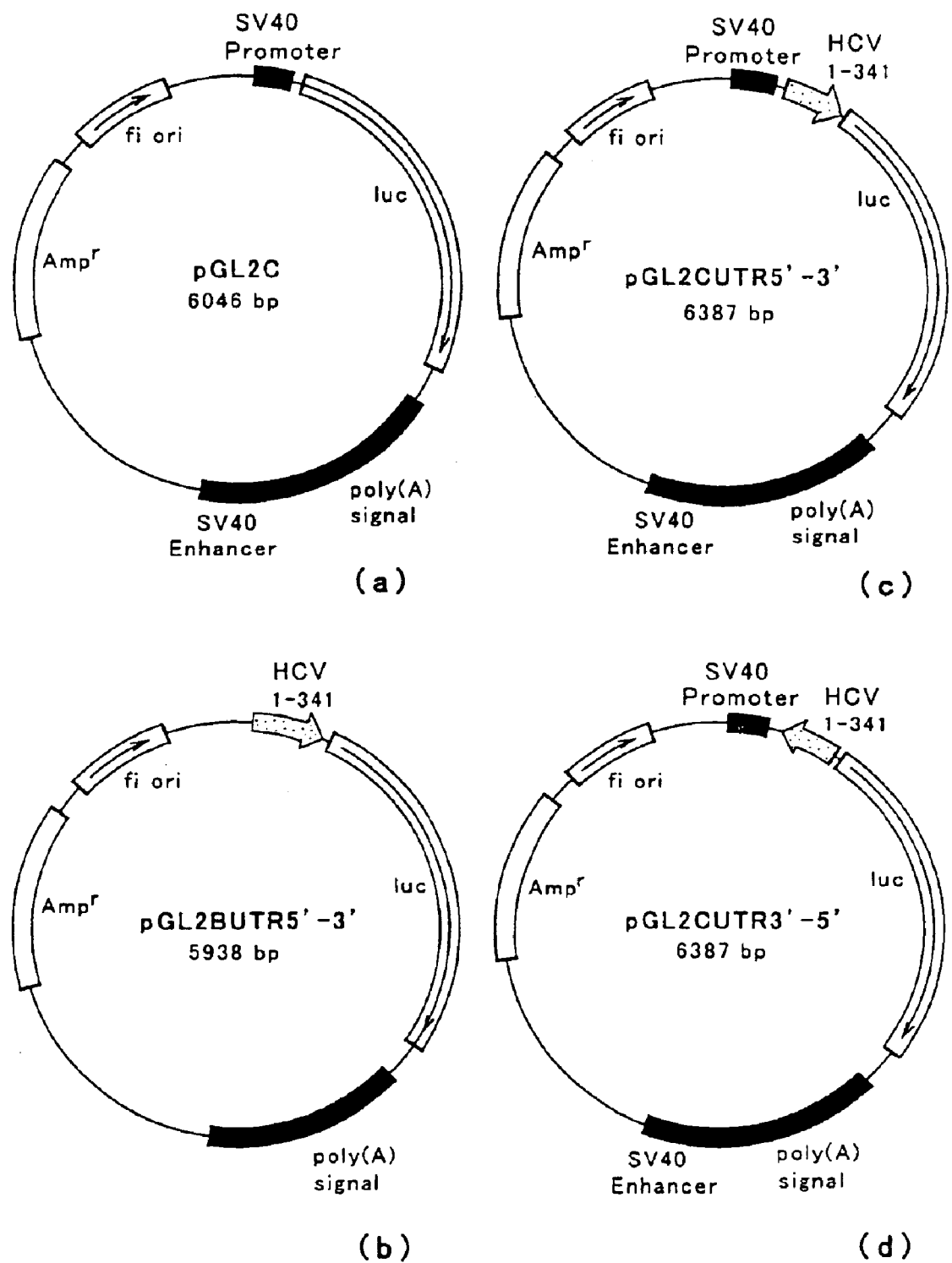
FIG. 2 shows diagrammatic representations of expression vectors comprising a nucleic acid sequence for enhancing expression of a useful gene according to one embodiment of the present invention.

Two vectors, i.e., pGL2B vector (i.e., pGL2Basic (Promega) containing SV40 polyA signal and cDNA sequences encoding firefly luciferase, without a promoter, an enhancer, and nucleic acid sequences for enhancing expression) and PGL2C vector (i.e., pGL2Control (Promega) containing firefly luciferase, SV40 polyA signal and an SV40 early promoter/enhancer, without nucleic acid sequences for enhancing expression; see, FIG. 2(*a*)) were respectively obtained, and pGL2B UTR5'–3' (pGL2B inserted with HCV1–341 obtained in Example 1 into the Hind III site in the 5'–3' direction; see FIG. 2(*b*)) was prepared as follows.

Among the cDNA fragments of HCV described above that are PCR products having a HindIII recognition site attached, HCV1–341 was selected and digested overnight at 37° C. using HindIII, and pGL2B vector was also digested with HindIII followed by treatment with alkaline phosphatase (Boehringer Mannheim) that was performed at 37° C. for 30 minutes in order to prevent from self-ligation within the molecules. The cDNA fragments were subjected to a ligation reaction to the vectors after digestion with HindIII, using the DNA Ligation Kit Ver.1 (Takara Shuzo Co., Ltd.) according to the manufacturer's protocol.

Thus obtained vector-DNA was introduced into competent cells to obtain transformed cells, thereafter, recombinant cells containing the HCV fragments were selected from the colonies, and plasmid DNAs were purified according to the standard technique.

For transfection, 5 µg of any one of the three kinds of vector-DNAs described above and 18.5 µl of CaCl$_2$ solution contained in the kit for transfection were placed into a tube, to which water was added to a final volume of 150 µl, thus, the tube A described above was prepared, while 150 µl of 2×HEPES was placed into the tube B. COS1 cells were used as the host cell, and transfection was performed according to the above-mentioned procedure, thereafter, luciferase activities were measured.

Since the pGL2B vector provides no luciferase activity, the enzyme solution obtained from the cells that were transfected with this vector was employed as a blank. The luciferase activities were represented as relative light units per milligram of protein (U/mg).

The results thus obtained are shown in the Table 1 below.

TABLE 1

| Vector | No. 1 (U/mg) | No. 2 (U/mg) |
|---|---|---|
| pGL2C | 1623 | 1616 |
| pGL2B UTR5'-3' | 60 | 52 |

These results indicate that the luciferase activity is very low in the host cells transfected with the pGL2B UTR5'-3' vector obtained by inserting HCV1-341 into the pGL2B vector comprising no promoter. It was therefore demonstrated that the 5'-untranslated region of the HCV gene (SEQ ID NO: 1; the nucleotide positions 1-341) itself exhibited no or little promoter activity, if any. In other words, there is no possibility that the 5'-untranslated region of HCV may be apparently and incorrectly estimated to have effects of promoting gene expression, due to the higher activity of the 5'-untranslated region of HCV as a promoter, than the promoter included in the vector that was used in Examples of the present invention. HCV is an RNA virus and is thus not converted into DNA during their replication cycle, therefore, it is quite reasonable that the no promoter activity is found in the 5'-untranslated region of its gene.

Example 3

Transient Transfection

In order to construct the useful gene expression vector according to the present invention, pGL2C UTR5'-3', pGL2C having HCV1-341 inserted into the Hind III site in the 5'-3' direction, (see, FIG. 2(c)) was prepared using HindIII in the similar manner to those described above in connection with the preparation of pGL2B UTR5'-3'.

COS1 cells ware transfected with 5 µg of either one of the vector-DNAs, pGL2C or pGL2C UTR5'-3' in the same manner as in Example 2, and luciferase activities were measured.

The results thus obtained are shown in the Table 2 below.

TABLE 2

| Vector | No. 1 (U/mg) | No. 2 (U/mg) |
|---|---|---|
| pGL2C | 1123 | 1360 |
| PGL2C UTR5'-3' | 4758 | 4637 |

The data clearly indicate that the luciferase activity is increased when HCV1-341 is inserted between the luciferase gene and the promoter sequence in the expression vector in the 5'-3' orientation. Thus, it was suggested that the 5'-untranslated region of the HCV gene has an effect of enhancing gene expression.

Example 4

Transient Transfection

Similar experiments to that described in Example 3 was also carried out except that pGL2C UTR3'-5', pGL2C having HCV1-341 inserted into the Hind III site in the 3'-5' direction opposite to the direction in Example 3, (see, FIG. 2(d)) was used instead of the pGL2C UTR5'-3' in Example 3.

The results are shown in the Table 3 below.

TABLE 3

| Vector | No. 1 (U/mg) | No. 2 (U/mg) |
|---|---|---|
| pGL2C | 177 | 197 |
| pGL2C UTR3'-5' | 156 | 96 |

As apparent from these results, no effect of enhancing activity is observed when HCV1-341 was inserted in the 3'-5' orientation, in contrast to the results in Example 3, rather, the activity was in fact reduced. Taking into account this result together with those obtained in Example 3, it is demonstrated that the 5'-untranslated region of HCV has the effect of enhancing expression of a useful gene product which is base sequence-specific and is dependent on the 5'-3' orientation. In addition, it is also apparent that this sequence is different in nature from any conventional enhancer sequences.

In this example, the level of activity observed in the cells into which pGL2C was transfected is as low as one tenth or less, compared to the levels obtained in Examples 2 and 3, it is believed that such a low level resulted from the transfection efficiency in this example that was 10-fold lower than those in Examples 2 and 3. Therefore, such a relative low level of activity should be considered to be trivial because a difference in effects between pGL2C and pGL2C UTR3'-5' vectors were examined.

Example 5

Transient Transfection

Figure 3:
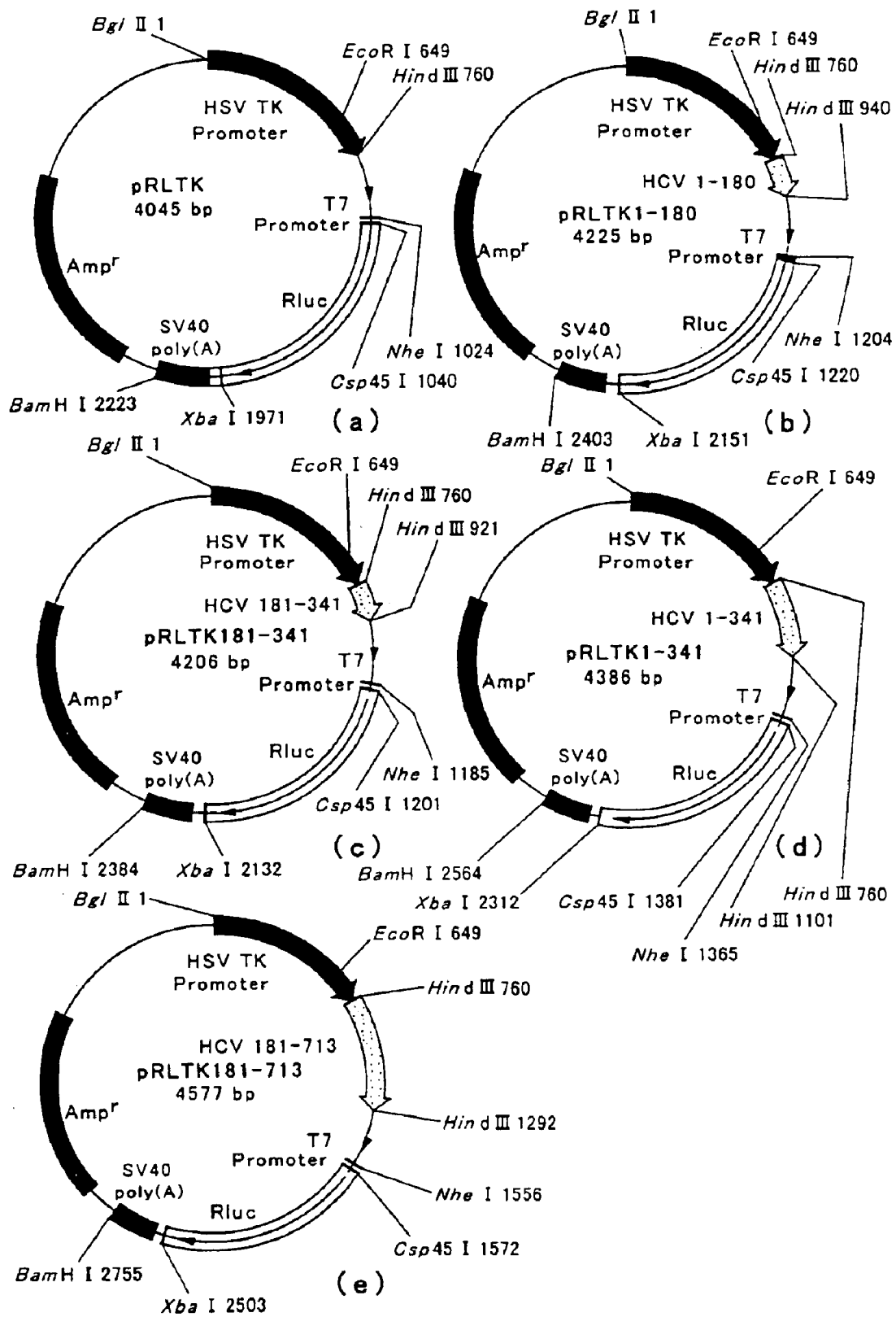
FIG. 3 shows diagrammatic representations of expression vectors comprising a nucleic acid sequence for enhancing expression of a useful gene according to another embodiment of the present invention.

In order to determine whether the effect of enhancing expression of a useful gene according to the present invention is specific to a promoter, a useful gene, a host cell or any combination thereof, a different promoter and pRLTK vector ((Promega), containing HSV TK promoter, SV40 polyA signal and Renilla Luciferase, see, FIG. 3(a)) containing luciferase derived from a different source from those used in Examples 2-4 were used in Ad this example, in addition, human hepatocarcinoma Hep G2 cells were used as the host cells.

The cDNA fragment comprising the 5'-untranslated region of HCV prepared in Example 1, HCV1-180, HCV1-341, HCV181-341 and HCV181-713 were inserted into the HindIII site of pRLTK in the same manner as described in Example 2 to generate pRLTK 1-180 (FIG. 3(b)), pRLTK 1-341 (FIG. 3(d)), pRLTK 181-341 (FIG. 3(c)), and pRLTK 181-713 (FIG. 3(e)), respectively. The pRLTK 1-341 has a nucleic acid sequence for enhancing expression inserted, which is same as the pGL2C UTR5'-3' in Example 3, while the pRLTK 1-180 has a sequence inserted which corresponds to the preceding half of the pRLTK 1-340, and the pRLTK 181-341 has a sequence inserted which corresponds to the latter half thereof. The pRLTK 181-713 contains a sequence that is 192 base pairs longer than the pRLTK 1-341, and these 192 base pairs correspond to the coding region of the core protein.

For transfection into the host cells, 5 µg of DNA per well was used as in Examples 2, 3, and 4, and the other conditions employed were also the same as in these examples.

However, Renilla-derived luciferase was used instead of luciferase derived from firefly in the above examples, accordingly, the Dual Luciferase Assay System was used as the assay kit as set forth above.

The activities observed in the host cells into which the vectors were transfected are shown the Table 4 below.

TABLE 4

| Vector | No. 1 (U/mg) | No. 2 (U/mg) | No. 3 (U/mg) |
|---|---|---|---|
| PRLTK | 21 | 65 | 42 |
| pRLTK 1–341 | 314 | 125 | 291 |
| pRLTK 1–180 | 227 | 175 | 164 |
| PRLTK 181–341 | 1,035 | 1,036 | 1,111 |
| PRLTK 181–713 | 482 | 381 | 491 |

As a result, the effect of accelerating the activities were remarkably exhibited with any one of sequences HCV1–180, HCV1–341, HCV181–341 and HCV181–713, therefore, it was demonstrated that the effect of accelerating the activities observed in Examples 2, 3, and 4 was not specific to the case where the SV40 promoter is used in combination with firefly luciferase and the vector was transfected into the COS1 cells. In addition, pRLTK 181–341 provided a strongest effect, suggesting that the effect by the nucleic acid sequence of the HCV1–341 may be resulted from the nucleotide positions 181–341 among the sequences.

Consequently, this example suggested that the 5'-untranslated region also (the sequence of the nucleotide positions 1–341 of SEQ ID NO: 1) has the effect of enhancing gene expression, regardless of difference in promoter as well as in type and source of the useful gene, or difference in host cell, and that among those sequences, the sequence that may be responsible for the effect according to the present invention may be present in the nucleotide positions 181–341, because the nucleotide positions 181–341 can provide the strongest effect. Further, it was also revealed that similar effects of enhancing expression could be obtained by using a portion of the coding region of the core protein (the nucleotide positions 342–713 of SEQ ID NO: 1) in addition to the 5'-untranslated region.

Example 6

Stable Cell Lines

Unlike Examples 2–5 where the effects of transient transfection in host cells were determined, the effect of the nucleic acid sequence for enhancing expression of a useful gene according to the present invention in stable cell lines that direct expression vectors to incorporate stably after transfection such that expression levels remain constant was determined in this example. The stable cell lines can be produced by transfecting the host cells with an expression vector including the neo gene that confers resistance to the antibiotic G418 (neomycin) and then harvesting the cells that can proliferate in a culture medium containing G418.

Figure 4:
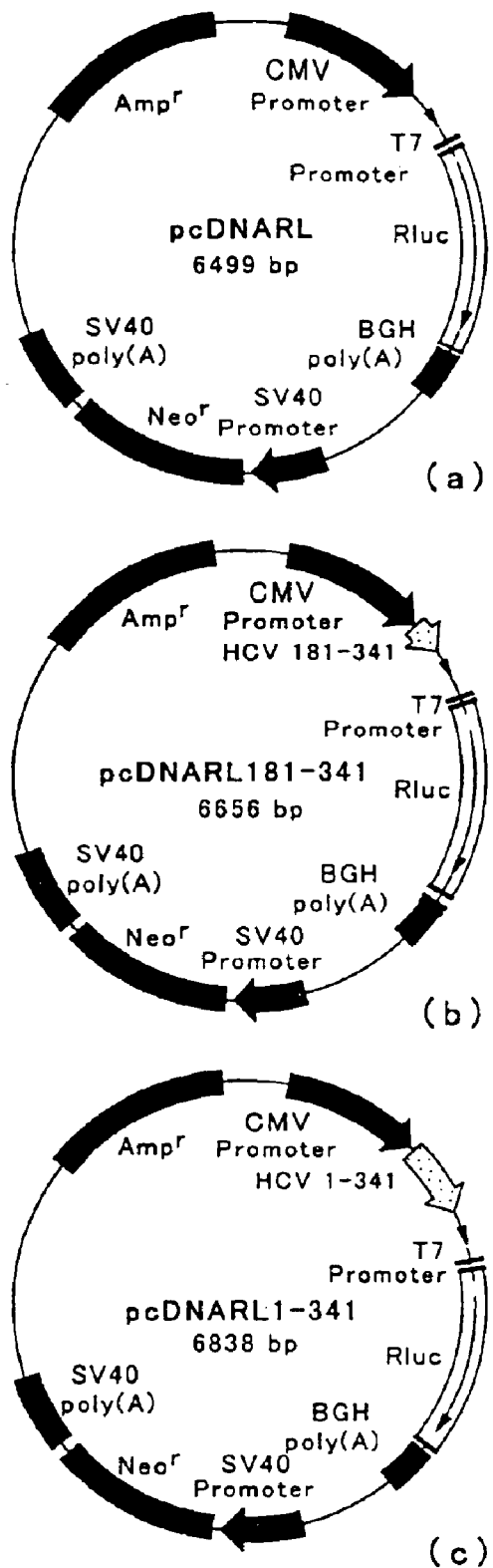
FIG. 4 shows diagrammatic representations of expression vectors comprising a nucleic acid sequence for enhancing expression of a useful gene according to yet another embodiment of the present invention.

First, pcDNA3.1+(Invitrogen) vector was obtained and the T7 promoter sequence was removed therefrom, to which HindIII/XbaI sites the Renilla luciferase as in Example 5 were incorporated, thus plasmid pcDNARL (FIG. 4(a)) was prepared. The promoter and enhancer of this expression vector are those derived from CMV, while the polyA signal is derived from bovine growth hormone.

The cDNA fragment HCV1–180, HCV1–341, HCV181–341, HCV181–713 or HCV1–713 was incorporated into the pcDNARL vector to prepare each plasmid pcDNARL 1–180, pcDNARL 1–341, pcDNARL 181–341, pcDNARL 181–713 or pcDNARL 1–713.

Transfection of these expression plasmids into host cells were performed in the same manner as in Example 2. In this case, a solution for the tube A was prepared of a final volume of 300 μl from 10 μg of vector-DNA and 37 μl of $CaCl_2$, and water contained in the kit, while the tube B was loaded with 300 μl of 2×HEPES. Further, the HepG2 cells as the host cells were prepared to the cell density of about 50% ($5\times10^6$ cells/20 mL medium) in a T75 flask (a tissue culture flask having an area of 75 $cm^2$ to which cells are adhered), the surface of which had previously been coated with collagen.

G418 was supplied to the culture medium at a concentration of 800 μg/ml, about 48 hours after the transfection in order to obtain stable cell lines, on the contrary to Examples 2–5 where the transfected cells were incubated for about 48 hours before measuring the luciferase activity. Almost all cells died during incubation at 37° C. for about 1 week but the cells containing the above-mentioned plasmid DNA(s) (having the resistance gene, neo) survived and formed colonies. After the colonies have grown to a sufficient size, they transferred into a fresh flask and were incubated at 37° C. and 5% $CO_2$ to effect proliferation, while portions of these cells were stored in liquid nitrogen.

As apparent, the colonies were harvested as a mixture of all colonies containing the survived cells rather than isolating the colonies prior to the proliferation, therefore, it can be speculated that the stable cell lines derived from different cDNA fragments were obtained under the same conditions.

An enzyme solution was prepared by extracting in the manner described above, from the cells of the stable cell lines, that are contained in the area corresponding to a single plate (35 mm in diameter) of the 6-well plate and the luciferase activity was then measured. The results are shown in the Table 5 below for pcDNARL, pcDNARL 1–341 (see FIG. 4(c)) and the pcDNARL 181–341 (see FIG. 4(b)).

TABLE 5

| Vector | No. 1 (U/mg) | No. 2 (U/mg) |
|---|---|---|
| PcDNARL | 69,593 | 66,062 |
| pcDNARL 1–341 | 89,987 | 86,442 |
| pcDNARL 181–341 | 198,413 | 201,365 |

As a result, it was indicated that the activity was also accelerated at the largest extent with the cDNA sequence of the HCV181–341 in the stable cell lines, as in Example 5. Moreover, although the promoter used in this experiment was different from those used in Examples 2–5, the effect of enhancing gene expression was also provided, accordingly, it was clearly suggested that the effect by the present invention are not provided in a specific promoter-dependent manner.

Therefore, the effect of enhancing the useful gene expression in the transient system was also observed in the permanent expression cells, thus, the doubt was withdrawn as to whether the expression activities were deemed to vary because the number of cells expressing luciferase was different among the groups subjected to comparison.

Example 7

Preparation and Sequencing of Nucleic Acid Sequence derived from HCV1b Mutant

Another cDNA sequence was prepared that comprises an IRES derived from the 5'-untranslated region of HCV1b. In the manner as described in Example 1, cDNA was synthesized from the serum of an HCV1b-positive patient that is different from the patient in Example 1. The patient in this example has suffered from hyperviremia ($10^9$ viral copies/ml plasma), with eminently extensive viral replication, accordingly, HCV may possibly be translated at a high efficiency in this patient. Using this cDNA as a template, PCR was performed using the primers of the following sequences (a sense primer having a HindIII site (underlined) at the 5'-end (SEQ ID NO: 8); and an antisense primer (SEQ ID NO: 9)) in order to amplify a fragment including the 5'-untranslated region of the HCV mutant.

cccaagcttgccagcccctgatgggggc (SEQ ID NO: 8)
ggtgcacggtctacgagacc (SEQ ID NO: 9)

The reaction conditions for PCR were same as those described in Example 1. The resulted PCR products were digested with Hind III and ApaL I, which were purified by agarose gel electrophoresis.

Figure 6:
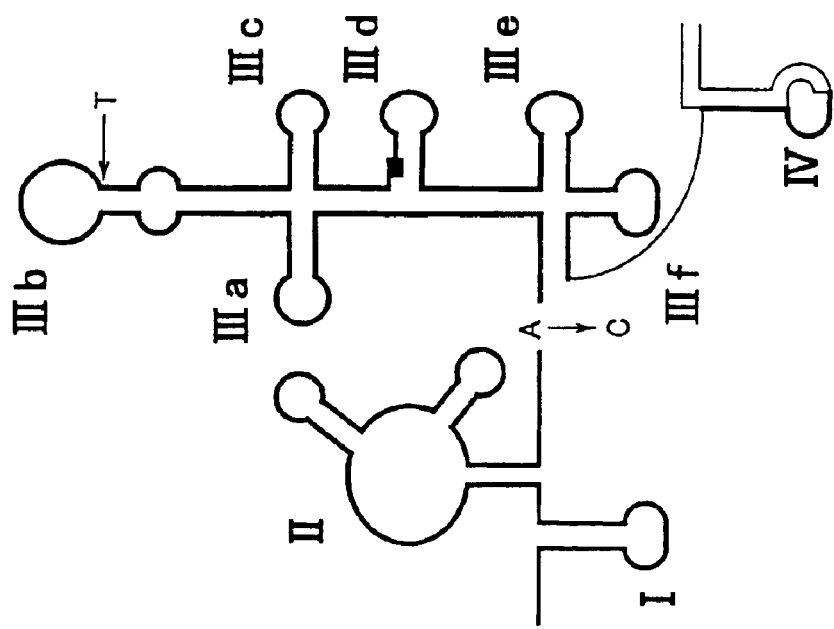
FIG. 6 is a schematic representation depicting mutation sites on the secondary structure in the 5'-untranslated region of a nucleic acid sequence derived from an HCV mutant.

Thus obtained fragment was sequenced according to the standard technique, thereby yielding the sequence comprising 342 nucleotides of SEQ ID NO: 7. When thus resulted sequence was compared with the above-mentioned fragment HCV1–341 (the nucleotide positions 1–341 of SEQ ID NO: 1) of the 5'-untranslated region derived from HCV1b (GenBank Accession Number: D00832) well known in the art, as shown in FIG. 5 as 5'-UTR$_{342}$ and 5'-UTR$_{341}$, in the 5'-untranslated region derived from a mutant, (1) adenine at the position 119 was substituted with cytosine; and (2) thymidine was inserted into the position 207. These mutations were also found in other cDNA clones derived from the same specimen. As shown in FIG. 6, the mutations thus identified within the ERES element were located in the area other than the highly conserved region, within or in the vicinity of the pyrimidine-rich tract, in the vicinity of the trans factor binding site, or in the vicinity of BoxA and BoxB.

Example 8

Construction of Vectors Comprising HCV1b-derived Sequence for Enhancing Expression In order to determine an effect of the fragment obtained in Example 7 on enhancement of expression, and an influence of the mutations in this fragment on the expression enhancement effect, a vector containing a T7 promoter, a sequence for enhancing expression (a fragment derived from the HCV 5'-untranslated region), a Renilla luciferase (Rluc) gene, and a T7 terminator was constructed from the pGEMEX-1 vector (Promega).

Rluc used was obtained as follows: The primers having the following sequences (a sense primer (SEQ ID NO: 10) having the Apa LI restriction site (underlined) at 5'-end and an antisense primer (SEQ ID NO: 11) having the Asc I restriction site (underlined) at 5'-end) were used to amplify pRL-TK (Promega), thereafter, the resulted PCR product was digested with ApaL I and Asc I and was then purified by agarose gel electrophoresis.

accgtgcaccatgacttcgaaagtttatga (SEQ ID NO: 10)
ttggcgcgccttattgttcatttttgagaa (SEQ ID NO: 11)

Figure 7:
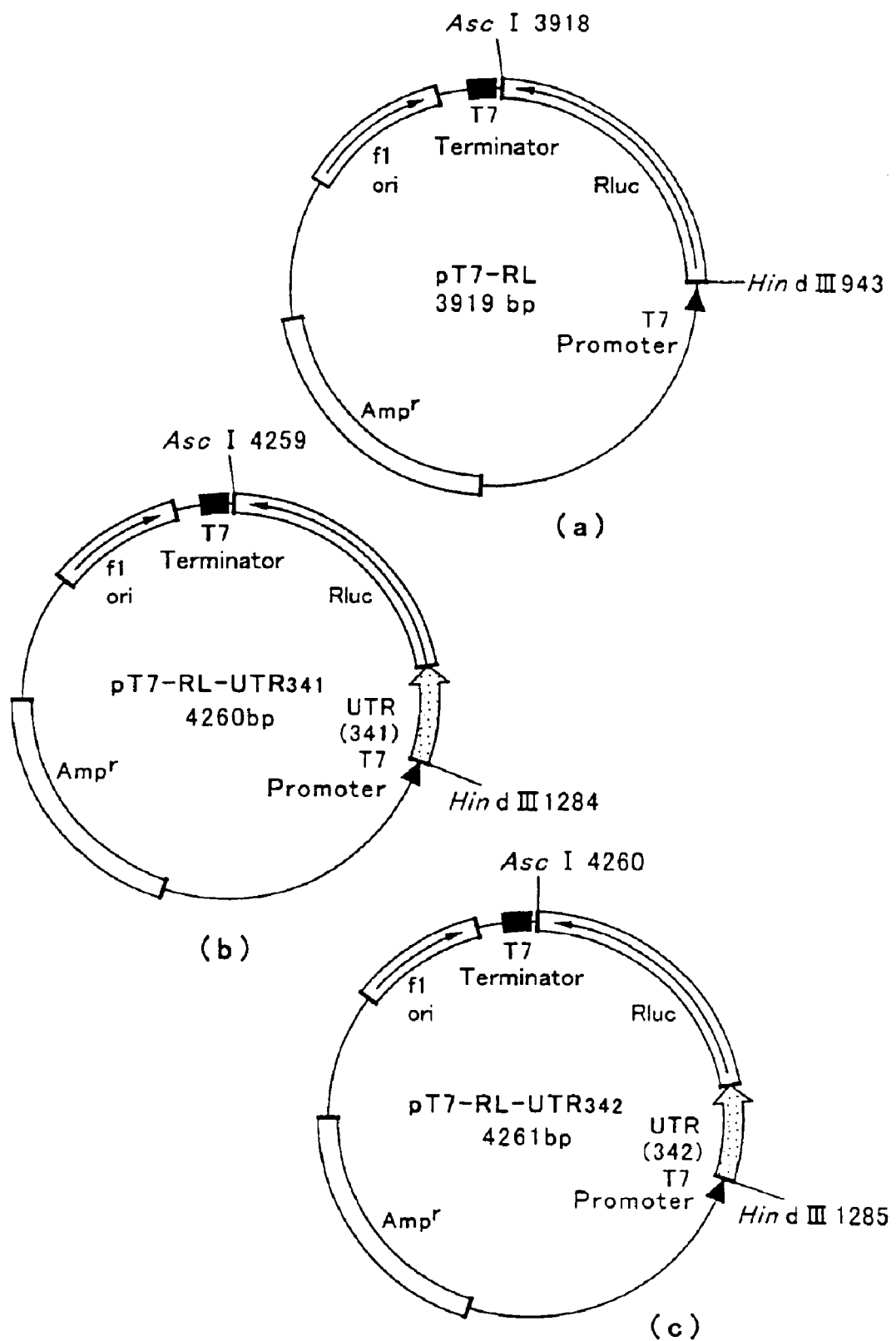
FIG. 7 shows diagrammatic representations of expression vectors comprising a nucleic acid sequence for enhancing expression of a useful gene according to yet another embodiment of the present invention.
Figure 8:
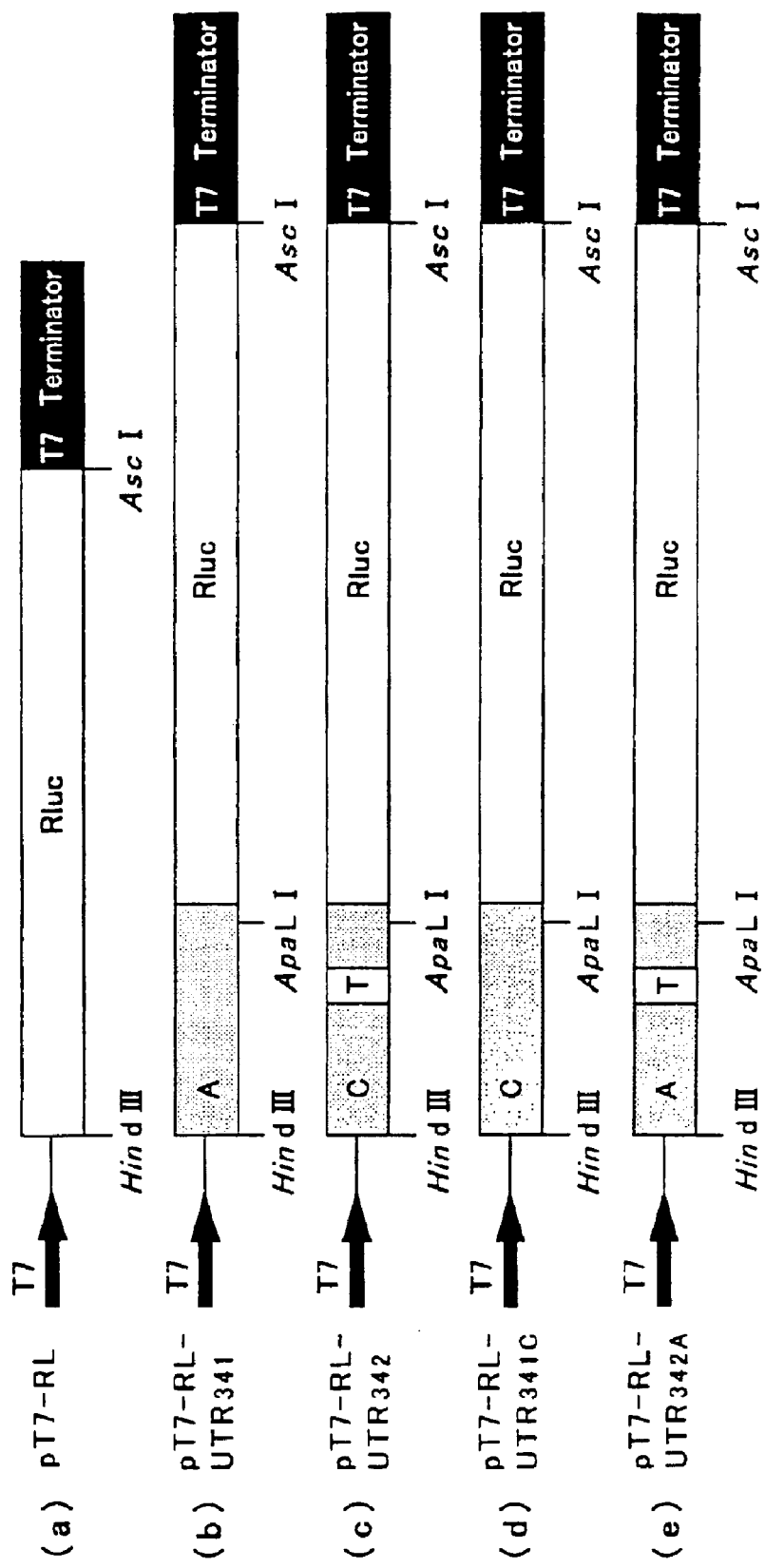
FIG. 8 shows schematic representations of expression vectors comprising a nucleic acid sequence for enhancing expression of a useful gene according to the embodiment in FIG. 7.

The vector pT7-RL-UTR$_{341}$, comprising HCV-341 has the structure shown in FIGS. 7 and 8(b), while the vector pT7-RL-UTR$_{342}$ comprising HCV-342 has the structure shown in FIG. 8(c).

Each of the vectors was prepared by previously removing entire T7 gene 10 sequence from the pGEMEX-1 vector and inserting the Hind III/Asc I restriction enzyme site between the T7 promoter and the T7 terminator thereof, which was ligated with either HCV-342 or HCV-341 (sequence for enhancing expression) along with Rluc in the similar manner described in Example 2. As the control vector pT7-RL containing no sequence for enhancing expression, the Rluc reporter gene was linked to the position immediately downstream of the T7 promoter and immediately upstream of the T7 terminator, as shown in FIGS. 7 and 8(a).

Furthermore, in order to determine an effect of substitution from adenine to cytosine at the position 119 of HCV-342, a vector pT7-RL-UTR$_{341C}$ (FIG. 8(d)) was prepared that has a sequence of HCV-341, of which position 119 was subjected to such a substitution, whilst, in order to determine an effect of insertion of thymidine into the position 207, a vector pT7-RL-UTR$_{342A}$ (FIG. 8(e)) was prepared that has a sequence of HCV-342, of which cytosine at position 119 was substituted by adenine. Vectors having these respective mutations were prepared in the same manner as described above, from those obtained by mutagenesis using PCR.

The PCR products introduced into the vectors were sequenced before use to verify that they have the desired sequence.

Example 9

Run-Off RNA Synthesis and in vitro Translation

The plasmid vector obtained in Example 8 was subjected to run-off RNA synthesis and in vitro translation as described below to express luciferase, thereby identifying an effect of the sequence for enhancing expression.

Each of the circular plasmid vectors was linearized by digesting with Asc I, and then each DNA was used as a template for run-off RNA synthesis by T7 RNA polymerase (Boehringer Mannheim). The conditions for transcription reaction were those provided by the manufacturer's protocol. After completing the transcription reaction, 10 U of RQ DNase I (Promega) was added to the reaction mixture to digest the template DNA, followed by extraction of RNA with phenol/chloroform mixture and precipitation with ethanol and 7.5 M sodium acetate. The concentration of the synthesized RNA was measured using a spectrophotometer.

Each of these RNAs was then translated in vitro in a nuclease-treated rabbit reticulocyte lysate (RRL; Promega). The translation reaction was proceeded at 30° C. for 90 minutes, using a reaction mixture containing 1 μg of RNA, 17.5 μl of the above-mentioned lysate, 10 U of RNase inhibitor (RNasin; Promega) and 20 μM of amino acid mixture (Promega) in a total volume of 25 μl, in the presence of 120 mM potassium chloride. Through addition of potassium chloride to keep a physiological salt concentration, the translation of HCV RNA can be perfected in an IRES-dependent manner. The reaction was then terminated by adding RNase A, and the luciferase activity was measured with 2.5 μl of the reaction mixture.

Figure 9:
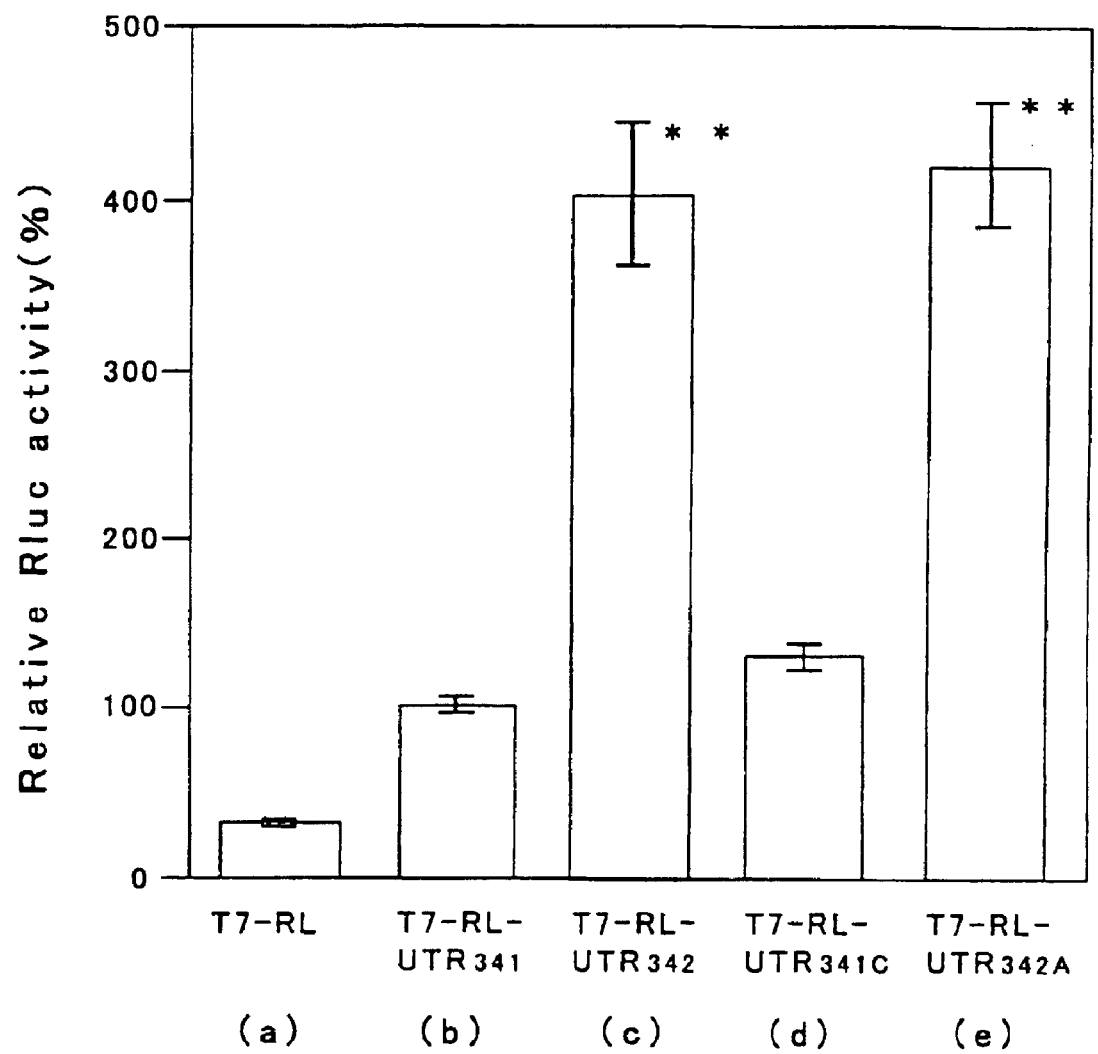
FIG. 9 is a graph illustrating the effects of enhancement of expression in an in vitro system using the vectors shown in FIGS. 7 and 8.

The results thus obtained are shown in FIG. 9. In this figure, the ordinate axis represents a percentage activity calculated for the vectors relative to that of pT7-RL-UTR$_{341}$ (b). These results represent the mean and standard deviation of twice-repeated triplet experiments. An asterisk (*) means a significant difference (p<0.01) from the result obtained by using pT7-RL-UTR$_{341}$ (b).

As apparent from FIG. 9, the vector pT7-RL-LTR$_{342}$ (c), into which the HCV-342 had been introduced as the sequence for enhancing expression, provided an activity that was nearly four times higher than the activity of the vector pT7-RL-UTR$_{341}$ (b) to which HCV-341 was incorporated.

In addition, because pT7-RL-UTR$_{341C}$ (d) provided an almost identical activity to the activity of the pT7-RL-UTR$_{341}$, it was suggested that the substitution at the position 119 of the HCV-342 may not be a mutation that can provide any effect on enhancement of expression. On the other hand, pT7-RL-UTR$_{342A}$ (e) provided a strong activity that was similar to the activity of the pT7-RL-UTR$_{342}$, therefore, it was speculated that the insertion of thymidine into the position 207 of the HCV-derived sequence of SEQ ID NO: 1 may be responsible for the IRES-dependent, strong ability of enhancing expression caused by the HCV-342.

Example 10

Transient Transfection

The effect of the enhancement of expression that is similar to the effect obtained in the in vitro system in Example 9 was also determined in the cells transfected with the vectors prepared in Example 8.

Hep G2 cell line was obtained from American Type Culture Collection (ATCC Accession No. HB-8065), incubated in Dulbecco's Modified Eagle Medium (DMEM) (GIBCO) supplemented with 10% fetal calf serum under a humid conditions in 5% CO$_2$. A cell line Hep T stably expressing T7 RNA polymerase was established by transfecting pAM8–1 (kindly provided by Dr. Nakanishi, Osaka University) into the Hep G2 cells.

Twenty-four hours before the transfection, the Hep T cells were seeded into a tissue culture dish of 35 mm in diameter, and then incubated under the same condition as of the Hep G2 cells. Seven μg each of plasmid DNA was used for transfection that was performed using the calcium phosphate precipitation method with Profection Mammalian Transfection System kit Promega). For the purpose of standardizing transfection efficiencies, the pGL3-Control vector (Promega) that express firefly luciferase was used along with each of the above-mentioned vectors in a molar ratio of 10:1 for co-transfection of both vectors. The co-transfection of each of the vectors was performed using triplicate wells respectively. Such triple-experiments were repeated twice.

Figure 10:
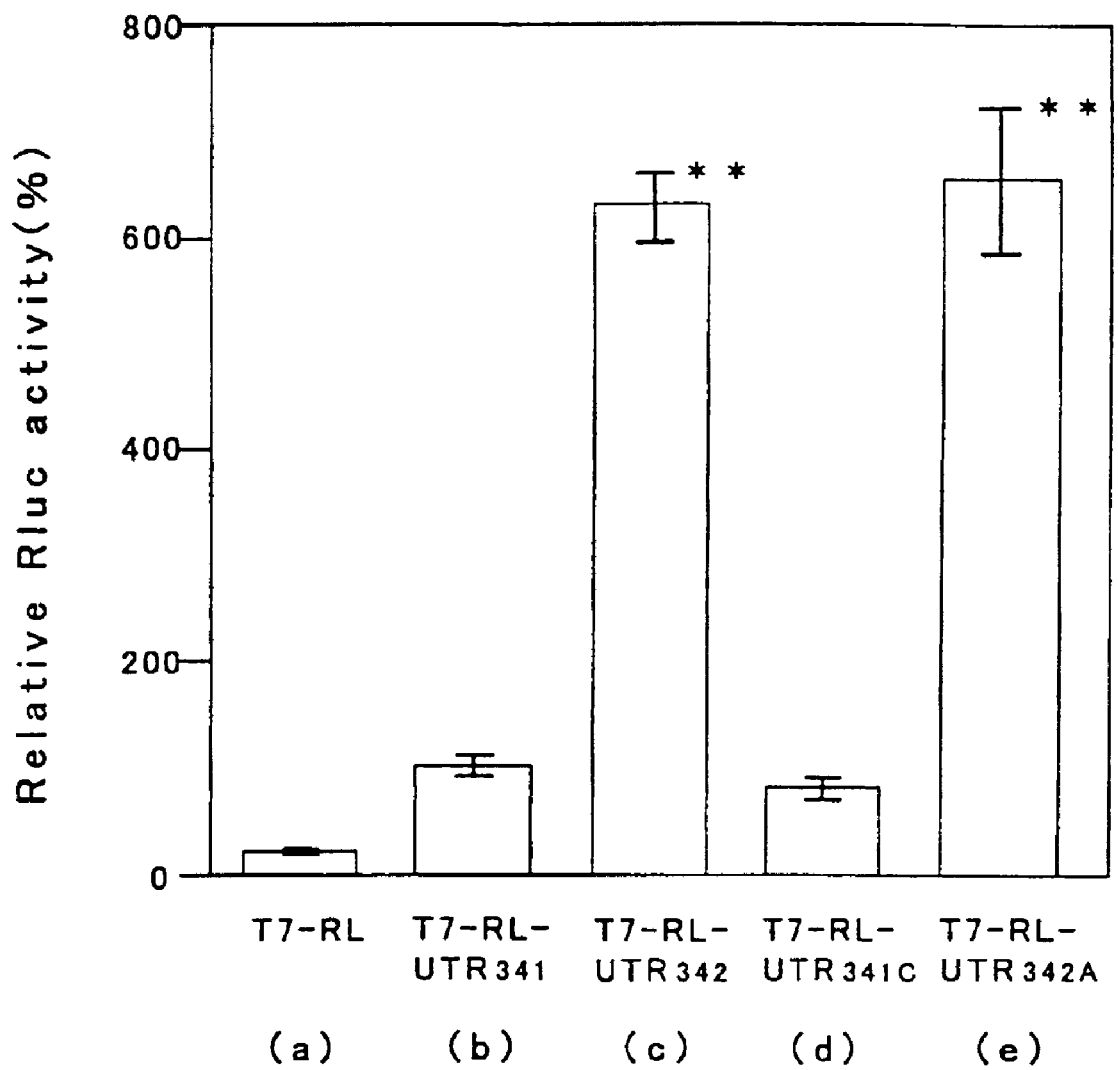
FIG. 10 is a graph illustrating effects on the enhancement of expression in Hep cells transfected with the vectors shown in FIGS. 7 and 8.

After 48 hours of incubation of thus transfected cells, luciferase activity in the cell lysate was measured using the Dual Luciferase Assay System. In addition, the co-transfected firefly luciferase was measured using the Luciferase Assay System to determine efficiency of transfection, with which the above-mentioned values indicating the activity were corrected. The results are shown in FIG. 10. In this figure, as in FIG. 9, the ordinate axis represents a percentage activity calculated for the vectors relative to that of pT7-RL-UTR$_{341}$ (b). The results represent the mean and standard deviation of twice-repeated triple-experiments. An asterisk (*) means a significant difference (p<0.01) from the result obtained in the pT7-RL-UTR$_{341}$ (b).

Similar effects to those obtained in Example 9 were indicated in FIG. 10. Namely, the vector pT7-RL-UTR$_{342}$ (c), into which the HCV-342 had been introduced as the sequence for enhancing expression, provided an activity that was nearly 6–7 times higher than the activity of the vector pT7-RL-UTR$_{341}$ (b) to which HCV-341 was incorporated. In addition, the pT7-RL-UTR$_{342A}$ (e) provided an activity that was similar to the activity of pT7-RL-UTR$_{342}$.

A significantly low Rluc activity was provided when the vector pT7-RL was transfected, presumably due to failure of efficient cap-independent initiation of translation.

Accordingly, it was demonstrated that the HCV-342 sequence as well as the sequence having a substitution at the position 119 of the HCV-342 could enhance expression either in an in vitro translation system or within the transfectants.

Example 11

Construction of Bicistronic Vectors Comprising HCV1b Variant-Derived Sequence for Enhancing Expression For the experiments to further exemplify the effects which were obtained in the above-mentioned monocistronic system, a vector having two cistrons was prepared that contains a similar sequence for enhancing expression to the vector prepared in Example 8. A vector which contains an SV40 promoter, a firefly luciferase (Fluc) gene, a sequence for enhancing expression, a Renilla luciferase (Rluc) gene and SV40 polyA was constructed from the pGL3 Control vector (Promega) to which the Fluc gene had been incorporated (see FIGS. 11 and 12).

Figure 11:
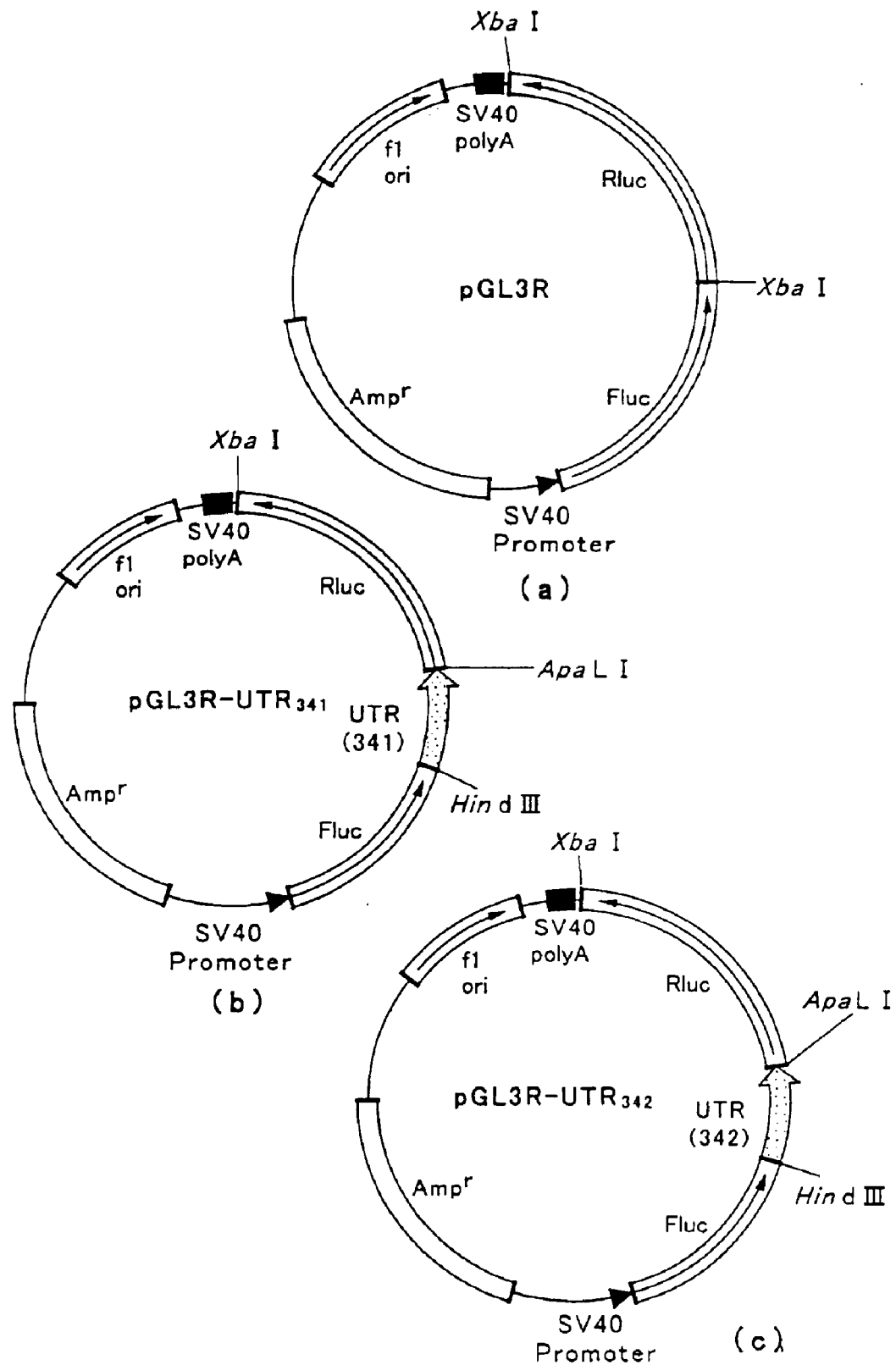
FIG. 11 shows schematic representations of bicistronic expression vectors comprising a nucleic acid sequence for enhancing expression of a useful gene according to another embodiment of the present invention.
Figure 12:
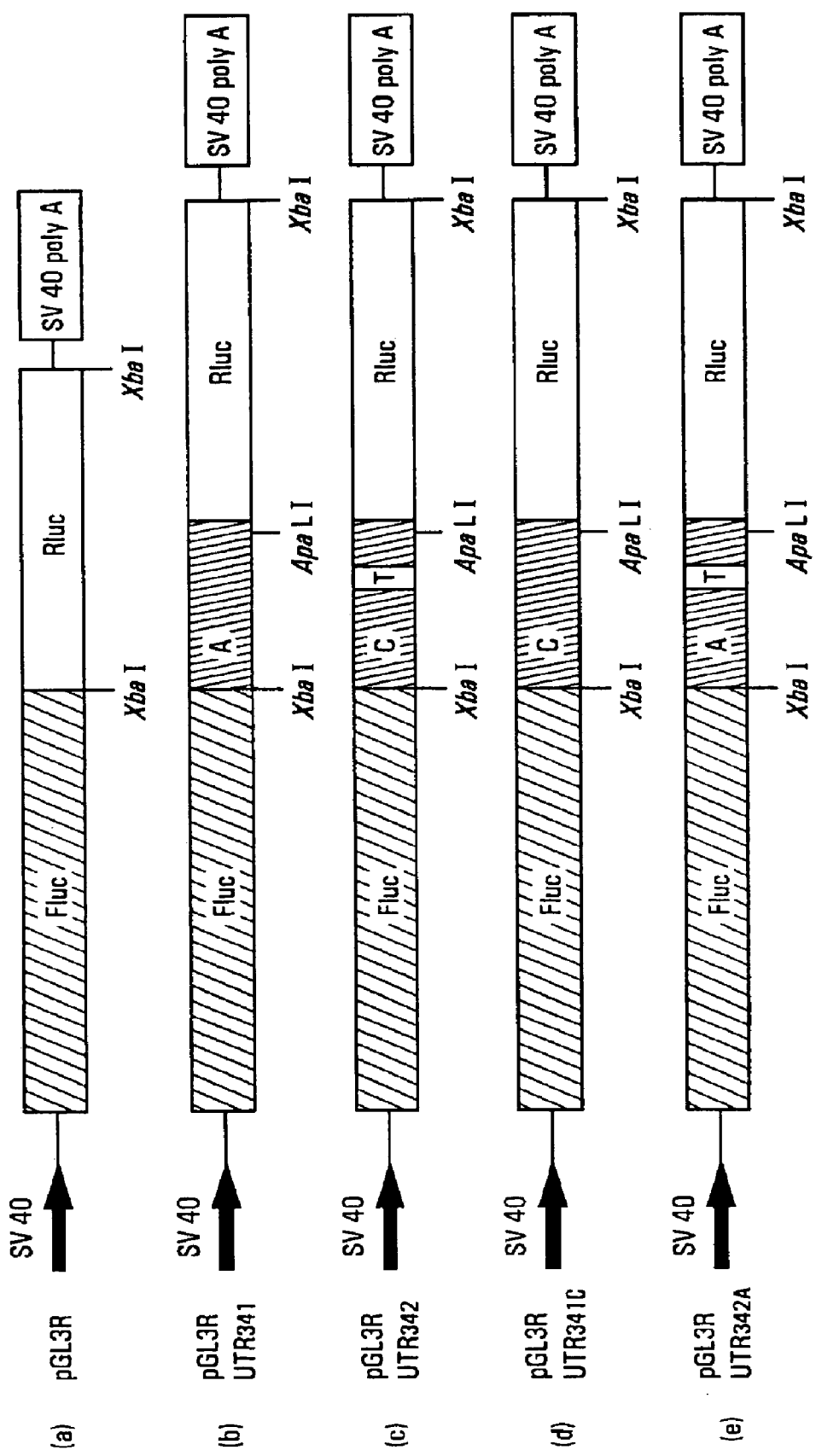
FIG. 12 shows schematic representations of bicistronic expression vectors comprising a nucleic acid sequence for enhancing expression of a useful gene according to the embodiment shown in FIG. 11.

Each of the sequences for enhancing expression (which are not contained in the control pGL3R; see, FIGS. 11 and 12(a)) that was amplified by PCR in the same manner as described in Example 8 and Rluc were introduced into the pGL3 Control vector at the Xba I site. The vector after the introduction was sequenced to verify that the individual sequences were incorporated in the correct direction.

Example 12

Transient Transfection

The bicistronic vector obtained in Example 11 was transfected into COS1 cells (obtained from ATCC, Accession No. CRL-1650) in the same manner as in Example 2.

Figure 13:
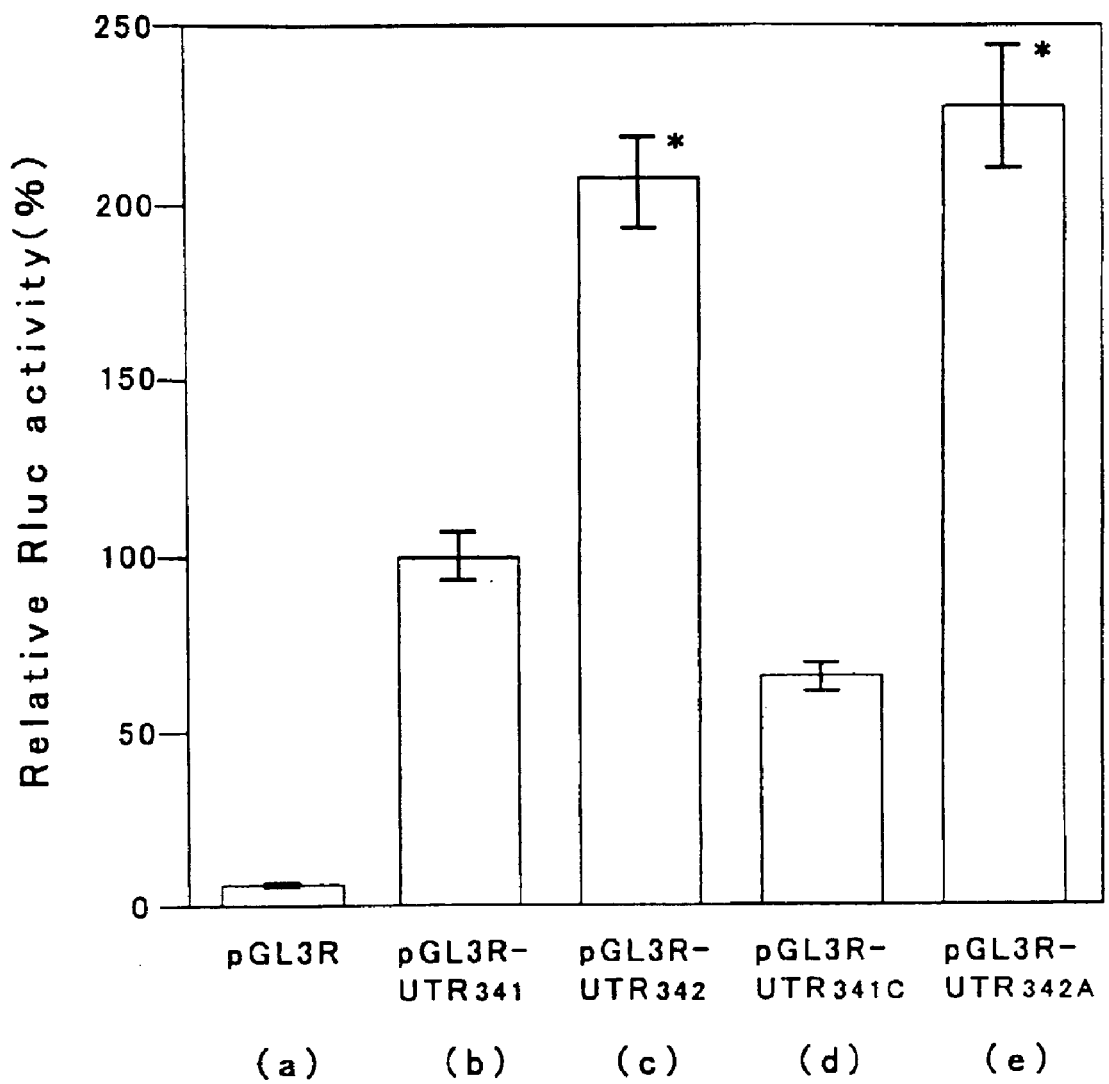
FIG. 13 is a graph illustrating effects on the enhancement of expression in COS cells transfected with the vectors shown in FIGS. 11 and 12.

Each of the values of the luciferase activity expressed in the transfectant was measured first using the Dual Luciferase Assay System, and then the activity of firefly luciferase expressed by the upstream cistrons were measured using the Luciferase Assay System to determine the efficiency of transfection, with which the above-mentioned values indicating the activity were corrected. The results are shown in FIG. 13. In this figure, similarly to FIG. 9, the ordinate axis represents a percentage activity calculated for the vectors relative to that of pGL3R-UTR$_{341}$ (b), and the results represent the mean and standard deviation of three times-repeated triple-experiments. An asterisk (*) means a significant difference (p<0.01) from the result obtained in the pGL3R-UTR$_{341}$ (b).

As shown in FIG. 13, the control vector pGL3R (a) provided almost no expression that was derived from the downstream second cistron (Rluc), while the activity was expressed only after the introduction of the sequence for enhancing expression. Further, the vector pGL3R-UTR$_{342}$ (c), into which the HCV-342 had been introduced as the sequence for enhancing expression, provided an activity that was nearly 2 times higher than the activity of the vector pGL3R-UTR$_{341}$ (b) to which HCV-341 was incorporated, or pGL3R-UTR$_{341C}$ (d) in which the position 119 of the HCV-341 was substituted. In addition, pGL3R-UTR$_{342A}$ (e) provided a strong activity that was similar to the activity of the pGL3R-UTR$_{342}$., therefore, it was again suggested that insertion of thymidine into the position 207 may promote the ability of enhancing expression whereas a mutation at the position 119 provides less effect on the enhancement of expression.

These results showed that a particularly excellent effect of enhancing expression based on the IRES activity caused by the sequence derived from the HCV mutant (5'-UTR342) is not cell-specific because such an effect can be obtained in cells other than hepatic cells, although some minor differences in the extent of the effects were found. In addition, it has been demonstrated that insertion of thymidine into the position 207 of the 5'-untranslated region of the wild-type HCV increases the effect of enhancing the expression, also in a cell-nonspecific manner.

The above-mentioned examples suggest that a single mutation introduced into the HCV-derived sequence for enhancing expression can significantly increase the effect of enhancing the expression. The mutation site which can lead to such an effect, that is, the position 207 of the 5'-untranslated region of the HCV gene is included in the region that is estimated as the binding site of the pyrimidine tract binding protein (Ali, N., and Siddiqul, A; *J. Virol.*, 69, 6367–6375, 1995). Since the pyrimidine tract binding protein is considered as a translation factor (Hellen, C. U. et al., *Proc. Natl. Acad. Sci. USA*, 90, 7642–7646, 1993; Witherell, G. W. et al., *Biochemistry*, 32, 8268–8275, 1993; Hellen, C. U. et al., *J. Virol.*, 68, 941–950, 1994; and Witherell, G. W., and Wimmer, E. *J Virol.*, 68, 3183–3192, 1994), it is supposed that the insertion of a single nucleotide into such a region may promote interaction between cellular factors required for the initiation of translation and the IRES. Enzymatic footprinting analyses demonstrated that polypeptide chain initiation factor eIF-3 may protect the nucleotide positions 204, 214, 215, 216 and 212 in domain III of the wild-type HCV IRES, suggesting that the eIF-3 binding sites on HCV IRES may be incorporated in the terminus of such domain III (Sizova, D. V. et al., *J. Virol.*, 72, 4775–4782, 1998). Because the position 207 locates at the center of the putative eIF-3 binding site, insertion of thymidine into this site is expected to be responsible for a change in affinity with eIF-3, thereby resulting in promotion of the effect of enhancing expression, however, details of this mechanism have not yet clarified. Comparing with the known 5'-UTR341, the novel 5'-UTR342 is speculated to exhibit a higher ability of enhancing IRES activities, probably due to: (1) existence of a mutation in the vicinity of the pyrimidine-rich tract; (2) existence of a mutation in the vicinity of the trans factor-binding site; or existence of a mutation in the vicinity of BoxA and BoxB, accordingly, a stronger ribosome binding may result in such enhancement.

Furthermore, since the novel HCV clinical isolate having a mutation at the 5'-untranslated region (SEQ ID NO: 7) has been isolated from serum of a patient suffering from hyperviremia, it is expected that viral replication of 5'-UTR342 may be extensive. Accordingly, characteristics of the infected HCV can be identified by specifically detecting 5'-UTR342 having thymidine inserted at position 207.

As apparent from the above Examples 2–6, the nucleic acid sequence for enhancing expression of a useful gene of the present invention could enhance luciferase expression even in different expression conditions using different methods of expression during the experiments performed for enhancement of luciferase expression in eukaryotic cells such as COS1 or HepG2 by using any one of SV40, HSV TK and CMV promoters which have affinity with eukaryotic RNA polymerase. It is known that translation in eukaryotic cells is cap-dependent and is IRES-independent. Therefore, the experimental systems described in Examples 2–6 can be comprehended as the ones based on the process of IRES activity-independent translation. Consequently, it is believed that the cause of effects of the nucleic acid sequence for enhancing expression of a useful gene of the present invention would be functions as an IRES activity-independent translation enhancement factor. In this regard, the present invention has verified for the first time that the 5'-UTR341 of HCV enhances expression of useful genes in experimental systems based on the process of IRES activity-independent translation.

On the other hand, as apparent from Example 9, in translation in vitro using rabbit reticulocyte lysate that is an experimental system based on the process of IRES activity-dependent translation, the 5'-UTR342 could enhance expression of useful genes by accelerating IRES activity at an larger extent as compared with the 5'-UTR341. Moreover, as apparent from Examples 10–12, luciferase expression was successfully enhanced, even in the cytoplasms of Hep T cells transformed by introducing T7 RNA polymerase into HepG2 cells, when the experiments were performed for enhancement of luciferase expression using the T7 promoter that has affinity with prokaryotic RNA polymerase. In addition, luciferase expression was also enhanced when the experiments were performed for enhancement of luciferase expression in T antigen-expressing COS cells, using SV40 promoter in a bicistronic system. Enhancement of the luciferase expression in the experimental systems based on the process of IRES activity-dependent translation as shown in Examples 9–12 may be presumed that it result from either acceleration of IRES activity of the 5'UTR-341 or from improvement of stability of mRNAs, with the 5'-UTR342 functioning as a cause of the effects. The present inventors have demonstrated that the 5'-UTR342 of HCV has not concerned improvement of mRNA stability by the primer extension assay (see *J. Virology*, 72, 8789–8796, 1998). In any case, expression of the useful gene can be enhanced using the 5'-UTR342 of HCV in an experimental system based on the process of IRES activity-dependent translation, as compared with the case using the 5'-UTR341. To Date, the 5'-UTR341 has been reported as having IRES activity in the experimental system based on the process of IRES activity-dependent translation in the HCV 5'-untranslated region (see, *Virology*, 226, 47–56, 1996; *J. Virology*, 72, 8789–8796, 1998). However, the present invention has first proven out that the novel, HCV-derived 5'-UTR342 sequence of the present invention accelerates IRES activity at a larger extent compared with the IRES activities of the 5'-UTR341 reported heretofore, thus resulting in enhancement of expression of useful genes.

It has been already reported that a useful gene (chloramphenicol acetyl transferase) can be expressed by ligating the HCV 5'-untranslated region at a region downstream of the T7 promoter in a monocistronic or bicistronic system as in Examples 9–12 and incorporating the useful gene into that downstream region (*Virology*, 226, 47–56, 1996; *J Virology*, 72, 8789–8796, 1998). However, all of these experiments were performed using the host cells in which the mammalian cells had previously been transformed with the HCV 5'-UTR341 such that T7 RNA polymerase is expressed as shown in Examples 10–12, according to the experimental system based on the process of IRES-dependent translation. In other words, although the HCV 5'-UTR341 has been verified as having IRES activities, no function as a translation enhancement factor has been indicated, that would be demonstrated by using experimental systems based on the process of IRES activation-independent translation. Accordingly, Examples 2–6 of the present invention have demonstrated for the first time the function of the translation enhancement factor. In addition, the present invention has also proven out for the first time that the novel, HCV-derived 5'-UTR342 can accelerate IRES activity in experimental systems based on the process of IRES activity-dependent translation, thus resulting in enhance expression of useful genes at a larger extent, as compared with the known 5'-UTR341.

INDUSTRIAL APPLICABILITY

The present invention provides the effect of enhancing gene expression in vivo and in vitro to increases the production of gene products, regardless of type of expression vectors, sequences to be comprised therein such as promoters, signals, and enhancers, type and source of a useful gene or type of host cells.

The sequence to be introduced may be subjected to a certain mutation(s) to further enhance the ability of enhancing gene expression.

These effects can be applied for the purpose of increasing the production of peptides in a cell culture system, as well as to vectors for effective gene therapies in combination with such a promoter that is specific to an internal organ or a tumor but has not been likely to come into practical use due to its low activity.

Additionally, it is possible to screen for substances (modulators, and the like) which can interact with IRESs, or for IRES-dependent translation initiators, using probes containing a sequence(s) having a higher IRES activity than ubiquitous IRES.

Moreover, translation of mRNA may be promoted by introducing the nucleic acid sequence for enhancing expression of a useful gene into a body of organisms, thereby treating diseases resulting from reduction of cap-dependent mRNA translation in the body of the organisms.

Alternatively, in order to treat diseases resulting from reduction of IRES activity in a body of organisms, the nucleic acid sequence for enhancing expression of a useful gene may be introduced into the body of organisms to promote translation of mRNA.

Furthermore, determination of severity of hepatitis C is permitted through detecting the presence of an HCV-derived specific polynucleotide sequence contained in a biological sample derived from a test subject.

What is claimed is:

1. An isolated polynucleotide for enhancing protein expression, wherein the polynucleotide comprises the continuous nucleic acid sequence consisting of nucleotides 181–341 of SEQ ID NO: 1 including one thymidine inserted between position 206 and 207 of SEQ ID NO: 1 and enhances protein expression when incorporated downstream of an expression regulatory promoter sequence and upstream of a protein coding sequence.

2. The isolated polynucleotide according to claim 1, which enhances said protein expression by increasing translation of the mRNA encoding said protein.

3. The isolated polynucleotide according to claim 1, which enhances said protein expression by increasing IRES activity.

4. An isolated polynucleotide consisting of the nucleotide sequence as set forth in SEQ ID NO: 7 over its entire length.

5. An expression vector comprising the isolated polynucleotide according to claim 1 or claim 4.

6. An isolated host cell transformed or transfected with the vector according to claim 5.

7. A method of expressing a protein in vitro, comprising the steps of:
   (a) transforming or transfecting an isolated host cell with an expression vector comprising both the isolated polynucleotide according to claim 1 or 4 and a protein coding sequence operably inserted downstream of the polynucleotide for enhancing protein expression, and
   (b) growing the host cell in a medium under conditions where the cell expresses the protein.

8. The method according to claim 7, wherein the method further comprises, after step (b), a step of isolating the protein from the cell and/or the growth medium.

9. A probe for screening substances that interact with IRES, comprising the polynucleotide according to claim 4, further comprising a detectable label.

10. A probe for screening IRES-dependent translation inhibitors, comprising the polynucleotide according to claim 4, further comprising a detectable label.

11. A composition comprising the isolated polynucleotide according to claim 1.

12. A composition comprising the isolated polynucleotide according to claim 4.

13. A method for determining a hypervirulent hepatitis C strain, comprising the steps of:
   (a) screening a biological sample for the presence of the polynucleotide according to claim 4, and;
   (b) determining presence or absence of the hypervirulent hepatitis C strain from the screening step, wherein the presence of the polynucleotide identifies the hypervirulent hepatitis C strain in the biological sample and the absence of said sequence indicates the absence of said hypervirulent hepatitis C.

14. An isolated polynucleotide according to claim 1, further comprising the continuous nucleotides consisting of nucleotides 1–180 of SEQ ID NO: 1.

15. An isolated polynucleotide according to claim 1 or 14, further comprising the continuous nucleotides consisting of nucleotides 342–713 of SEQ ID NO: 1.

16. The isolated polynucleotide according to claim 1 or 4 which further comprises continuous nucleotides for enhancing protein expression, wherein a 5'-untranslated region of the continuous nucleotides comprises a nucleotide sequence corresponding to at least one region selected from the group consisting of pyrimidine-rich tract, Box A, Box B, a trans factor-binding site, and a combination thereof.

17. The isolated polynucleotide according to claim 16, wherein the 5'-untranslated region comprises an AUG or ATG sequence.

18. The isolated polynucleotide according to claim 16, wherein the 5'-untranslated region comprises a part or an entire region of IRES of viral mRNA.

19. The isolated polynucleotide according to claim 16, wherein said continuous nucleotides further comprises a portion of a coding region taken from a viral gene adjacent to the 5'-untranslated region.

20. The isolated polynucleotide according to claim 4, wherein said nucleotide sequence is a cDNA sequence.

21. An expression vector according to claim 5, further comprising a protein coding sequence operably inserted downstream of the polynucleotide for enhancing protein expression.

22. An expression vector comprising a promoter sequence, a protein coding sequence and the nucleotide sequence set out in SEQ ID NO: 7 over its entire length incorporated downstream of the promoter sequence and upstream of protein coding sequence, wherein the nucleotide sequence enhances expression of the protein coding region by means of increasing IRES activity.

23. The expression vector according to claim 22, which is a vector for expression in eukaryotic cells.

* * * * *

UNITED STATES PATENT AND TRADEMARK OFFICE
CERTIFICATE OF CORRECTION

PATENT NO.      : 6,869,779 B1
DATED           : March 22, 2005
INVENTOR(S)     : Osami Yamada et al.

It is certified that error appears in the above-identified patent and that said Letters Patent is hereby corrected as shown below:

<u>Title page,</u>
Item [22], PCT Filed, "July 7" should be -- July 8 --;
Item [57], ABSTRACT,
Line 2, "car" should be -- can --.

Signed and Sealed this

Thirtieth Day of August, 2005

JON W. DUDAS
*Director of the United States Patent and Trademark Office*

SEQUENCE LISTING

```
<160> NUMBER OF SEQ ID NOS:  11

<210> SEQ ID NO 1
<211> LENGTH: 713
<212> TYPE: DNA
<213> ORGANISM: Hepatitis Type C Virus (HCV)
<220> FEATURE:
<221> NAME/KEY: 5'UTR
<222> LOCATION: (1)..(341)
<221> NAME/KEY: CDS
<222> LOCATION: (342)..(713)

<400> SEQUENCE: 1
gccagccccc tgatgggggc gacactccac catagatcac tccctgtga ggaactactg      60 tcttcacgca gaaagcgtct agccatggcg ttagtatgag tgtcgtgcag cctccaggac    120 ccccctccc gggagagcca tagtggtctg cggaaccggt gagtacaccg gaattgccag    180
gacgaccggg tcctttcttg gatcaaccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac c atg agc aca aat cct    356
                                              Met Ser Thr Asn Pro
                                                1               5 aaa cct caa aga aaa acc aaa cgt aac acc aac cgc cgc cca cag gac     404
Lys Pro Gln Arg Lys Thr Lys Arg Asn Thr Asn Arg Arg Pro Gln Asp
             10                  15                  20 gtc aag ttc ccg ggc ggt ggt cag atc gtt ggt gga gtt tac ctg ttg     452
Val Lys Phe Pro Gly Gly Gly Gln Ile Val Gly Gly Val Tyr Leu Leu
         25                  30                  35 ccg cgc agg ggc ccc agg ttg ggt gtg cgc gcg act agg aag act tcc     500
Pro Arg Arg Gly Pro Arg Leu Gly Val Arg Ala Thr Arg Lys Thr Ser
     40                  45                  50 gag cgg tcg caa cct cgt gga agg cga caa cct atc ccc aag gct cgc     548
Glu Arg Ser Gln Pro Arg Gly Arg Arg Gln Pro Ile Pro Lys Ala Arg
 55                  60                  65 cgg ccc gag ggc agg acc tgg gct cag ccc ggg tat cct tgg ccc ctc     596
Arg Pro Glu Gly Arg Thr Trp Ala Gln Pro Gly Tyr Pro Trp Pro Leu
 70                  75                  80                  85 tat ggc aac gag ggc atg ggg tgg gca gga tgg ctc ctg tcg ccc cgc     644
```

```
                                   -continued

Tyr Gly Asn Glu Gly Met Gly Trp Ala Gly Trp Leu Leu Ser Pro Arg
             90                  95                 100 ggc tcc cgg cct agt tgg ggc cct tcg gac ccc cgg cgt agg tcg cgt        692
Gly Ser Arg Pro Ser Trp Gly Pro Ser Asp Pro Arg Arg Ser Arg
            105                 110                 115 aat ttg ggt aag gtc atc gat                                             713
Asn Leu Gly Lys Val Ile Asp
        120

<210> SEQ ID NO 2
<211> LENGTH: 31
<212> TYPE: DNA
<213> ORGANISM: Hepatitis Type C Virus (HCV)
<220> FEATURE:
<223> OTHER INFORMATION: Nucleotide Sequence of PCR Primer for
      Amplifying Fragments of HCV cDNA

<400> SEQUENCE: 2
cccaagcttg ccagccccct gatgggggcg a                                      31

<210> SEQ ID NO 3
<211> LENGTH: 31
<212> TYPE: DNA
<213> ORGANISM: Hepatitis Type C Virus (HCV)
<220> FEATURE:
<223> OTHER INFORMATION: Nucleotide Sequence of PCR Primer for
      Amplifying Fragments of HCV cDNA

<400> SEQUENCE: 3
cccaagcttc tggcaattcc ggtgtactca c                                      31

<210> SEQ ID NO 4
<211> LENGTH: 29
<212> TYPE: DNA
<213> ORGANISM: Hepatitis Type C Virus (HCV)
<220> FEATURE:
<223> OTHER INFORMATION: Nucleotide Sequence of PCR Primer for
      Amplifying Fragments of HCV cDNA

<400> SEQUENCE: 4
cccaagcttg acgaccgggt cctttcttg                                         29

<210> SEQ ID NO 5
<211> LENGTH: 30
<212> TYPE: DNA
<213> ORGANISM: Hepatitis Type C Virus (HCV)
<220> FEATURE:
<223> OTHER INFORMATION: Nucleotide Sequence of PCR Primer for
      Amplifying Fragments of HCV cDNA

<400> SEQUENCE: 5
cccaagcttg gtgcacggtc tacgagacct                                        30

<210> SEQ ID NO 6
<211> LENGTH: 26
<212> TYPE: DNA
<213> ORGANISM: Hepatitis Type C Virus (HCV)
<220> FEATURE:
<223> OTHER INFORMATION: Nucleotide Sequence of PCR Primer for
      Amplifying Fragments of HCV cDNA

<400> SEQUENCE: 6
cccaagctta tcgatgacct taccca                                            26

<210> SEQ ID NO 7
<211> LENGTH: 342
```

-continued

<212> TYPE: DNA
<213> ORGANISM: Mutated Hepatitis Type C1b Virus (HCV)
<220> FEATURE:
<221> NAME/KEY: 5'UTR
<222> LOCATION: (1)..(342)

<400> SEQUENCE: 7
gccagccccc tgatgggggc gacactccac catagatcac tcccctgtga ggaactactg 60
tcttcacgca gaaagcgtct agccatggcg ttagtatgag tgtcgtgcag cctccaggcc 120
ccccctcccc gggagagcca tagtggtctg cggaaccggt gagtacaccg gaattgccag 180
gacgaccggg tcctttcttg gatcaatccc gctcaatgcc tggagatttg ggcgtgcccc 240
cgcgagactg ctagccgagt agtgttgggt cgcgaaaggc cttgtggtac tgcctgatag 300
ggtgcttgcg agtgccccgg gaggtctcgt agaccgtgca cc 342

<210> SEQ ID NO 8
<211> LENGTH: 29
<212> TYPE: DNA
<213> ORGANISM: Hepatitis Type C1b Virus (HCV)
<220> FEATURE:
<223> OTHER INFORMATION: Nucleotide Sequence of PCR Sense Primer for Amplifying Mutated Fragments of HCV1b cDNA

<400> SEQUENCE: 8
cccaagcttg ccagccccct gatgggggc 29

<210> SEQ ID NO 9
<211> LENGTH: 20
<212> TYPE: DNA
<213> ORGANISM: Hepatitis Type C1b Virus (HCV)
<220> FEATURE:
<223> OTHER INFORMATION: Nucleotide Sequence of PCR Anti-sense Primer for Amplifying Mutated Fragments of HCV1b cDNA

<400> SEQUENCE: 9
ggtgcacggt ctacgagacc 20

<210> SEQ ID NO 10
<211> LENGTH: 30
<212> TYPE: DNA
<213> ORGANISM: Renilla luciferase
<220> FEATURE:
<223> OTHER INFORMATION: Nucleotide Sequence of PCR Sense Primer for Amplifying Renilla luciferase gene

<400> SEQUENCE: 10
accgtgcacc atgacttcga aagtttatga 30

<210> SEQ ID NO 11
<211> LENGTH: 30
<212> TYPE: DNA
<213> ORGANISM: Renilla luciferase
<220> FEATURE:
<223> OTHER INFORMATION: Nucleotide Sequence of PCR Anti-sense Primer for Amplifying Renilla luciferase gene

<400> SEQUENCE: 11
ttggcgcgcc ttattgttca tttttgagaa 30